US008003325B2

(12) United States Patent
Ansell et al.

(10) Patent No.: US 8,003,325 B2
(45) Date of Patent: Aug. 23, 2011

(54) POLYMORPHISMS OF THE BLYS GENE AND USE IN DIAGNOSTIC METHODS

(75) Inventors: Stephen M. Ansell, Rochester, MN (US); Anne J. Novak, Oronoco, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 104 days.

(21) Appl. No.: 12/323,861

(22) Filed: Nov. 26, 2008

(65) Prior Publication Data

US 2009/0253135 A1 Oct. 8, 2009

Related U.S. Application Data

(60) Provisional application No. 60/991,509, filed on Nov. 30, 2007.

(51) Int. Cl.
C12Q 1/68 (2006.01)
C12P 19/34 (2006.01)
C07H 21/02 (2006.01)
C07H 21/04 (2006.01)

(52) U.S. Cl. .......... 435/6; 435/91.2; 536/23.1; 536/24.3

(58) Field of Classification Search .................... None
See application file for complete search history.

(56) References Cited

U.S. PATENT DOCUMENTS

| RE30,985 E | 6/1982 | Cartaya |
| 4,399,216 A | 8/1983 | Axel et al. |
| 4,551,433 A | 11/1985 | DeBoer |
| 4,560,655 A | 12/1985 | Baker |
| 4,657,866 A | 4/1987 | Kumar |
| 4,745,051 A | 5/1988 | Smith et al. |
| 4,767,704 A | 8/1988 | Cleveland et al. |
| 4,837,148 A | 6/1989 | Cregg |
| 4,927,762 A | 5/1990 | Darfler |
| 4,929,555 A | 5/1990 | Cregg et al. |
| 5,445,934 A | 8/1995 | Fodor et al. |
| 5,591,639 A | 1/1997 | Bebbington |
| 5,631,734 A | 5/1997 | Stern et al. |
| 5,641,670 A | 6/1997 | Treco et al. |
| 5,654,173 A | 8/1997 | Jacobs et al. |
| 5,658,759 A | 8/1997 | Bebbington |
| 5,733,761 A | 3/1998 | Treco et al. |

FOREIGN PATENT DOCUMENTS

| EP | 0 155 476 | 9/1985 |
| EP | 0 036 776 | 5/1988 |
| EP | 0 127 839 | 7/1992 |
| EP | 0 244 234 | 7/1993 |
| WO | WO 87/00195 | 1/1987 |
| WO | WO 91/00357 | 1/1991 |
| WO | WO 94/16101 | 7/1994 |
| WO | WO 95/35505 | 12/1995 |
| WO | WO 97/27317 | 7/1997 |
| WO | WO 99/15650 | 4/1999 |
| WO | WO 2007/053732 | 5/2007 |

OTHER PUBLICATIONS

Novak et al. (Cancer Research 2009 vol. 69 p. 4217).*
Ansell et al. (American Journal of Hematology 2009 vol. 84 p. 71).*
GenBank Accession No. NM_003808, dated Mar. 29, 2009.
GenBank Accession No. NM_033622, dated Mar. 29, 2009.
GenBank Accession No. NM_052945, dated Mar. 29, 2009.
GenBank Accession No. NM_172087, dated Mar. 29, 2009.
GenBank Accession No. NM_172088, dated Mar. 29, 2009.
Database accession No. Pr004913251.1, dated Mar. 6, 2006.
Database accession No. ss76834769, dated Aug. 27, 2007.
Ansell et al., "B-lymphocyte stimulator (BLyS) is highly expressed in Waldenstrom's macroglobulinemia," *Blood*, 2004, 104(11):630A, Abstract 2291.
Ballance et al., "Transformation of *Aspergillus nidulans* by the orotidine-5'-phosphate decarboxylase gene of *Neurospora crassa*," *Biochem. Biophys. Res. Commun.*, 1983, 112:284-289.
Barnes and Sato, "Methods for Growth of Cultured Cells in Serum-Free Medium," *Anal. Biochem.*, 1980, 102:255-270.
Beach et al., "Functionally homologous cell cycle control genes in budding and fission yeast," *Nature*, 1982, 300:706-709.
Beaucage and Caruthers, "Deoxynucleoside phosphoramidites—a new class of key intermediates for deoxypolynucleotide synthesis," *Tet. Letters*, 1981, 22:1859.
Boshart et al., "A very strong enhancer is located upstream of an immediate early gene of human cytomegalovirus," *Cell*, 1985, 41:521-530.
Briones et al., "BLyS and BLyS receptor expression in non-Hodgkin's lymphoma," *Exp. Hematol.*, 2002, 30(2):135-141.
Carbonell et al., "Synthesis of a gene coding for an insect-specific scorpion neurotoxin and attempts to express it using baculovirus vectors," *Gene*, 1988, 73(2):409-418.
Chadwick et al., "Heterozygote and Mutation Detection by Direct Automated Fluorescent DNA Sequencing Using a Mutant Taq DNA Polymerase," *Biotechniques*, 1996, 20:676-683.
Chalifour et al., "A Method for Analysis of Gene Expression Patterns," *Anal. Biochem.*, 1994, 216:299-304.

(Continued)

*Primary Examiner* — Katherine Salmon
(74) *Attorney, Agent, or Firm* — Fish & Richardson P.C.

(57) ABSTRACT

The present invention provides an isolated polynucleotide comprising at least one polymorphic nucleotide sequence, for example, the major alleles of the SNPs described as rs12583006, rs1224141, and rs1248930 and diagnostic assays for detecting the presence of these polymorphism associated with a condition associated with BLyS activity, such as hematological malignancy including B cell malignancies. The diagnostic assays are useful in predicting an individual's likelihood of developing a condition associated with BLyS activity, such as hematological malignancies, and for methods for treating an individual clinically diagnosed with a condition associated with BLyS activity, such as prediction of a patient's likelihood to respond to a specific drug treatment. The invention also provides an array of nucleic acid molecules immobilized on a solid surface, where at least one of the nucleic acid molecules comprises a BLyS polymorphic nucleic acid molecule. The nucleic acid arrays of the invention allow rapid detection of hybridizing nucleic acid-molecules, in a nucleic acid sample from an individual, of a BLyS polymorphism associated with hematological malignancy.

8 Claims, No Drawings

OTHER PUBLICATIONS

Chang et al., "Phenotypic expression in *E. coli* of a DNA sequence coding for mouse dihydrofolate reductase," *Nature*, 1978, 275:617-624.
Chee et al., "Accessing Genetic Information with High-Density DNA Arrays," *Science*, 1996, 274:610-613.
Clare et al., "Cloning and characterization of the ribosomal RNA genes of the dimorphic yeast, *Yarrowia lipolytica*," *Curr. Genet.*, 1986, 10:449-452.
Cohen et al., "Emerging Technologies for Sequencing Antisense Oligonucleotides: Capillary Electrophoresis and Mass Spectrometry," *Adv. Chromatography*, 1996, 36:127-162.
Coutelle, "New DNA-analysis techniques (Minireview)," *Biomed. Biochim Acta*, 1991, 50:3-10.
Cregg et al., "*Pichia pastoris* as a Host System for Transformations," *Mol. Cell. Biol.*, 1985, 5:3376.
Cronin et al., "Cystic Fibrosis Mutation Detection by Hybridization to Light-Generated DNA Probe Arrays," *Human Mutation*, 1996, 7:244-255.
Das et al., "Transformation of *Kluyveromyces fragilis*," *J. Bacteriol.*, 1984, 158:1165-1167.
DeBoer et al., "The tac promoter: a functional hybrid derived from the trp and lac promoters," *Proc. Natl. Acad. Sci. USA*, 1983, 80:21-25
Delahunty et al., "Testing the feasibility of DNA typing for human identification by PCR and an oligonucleotide ligation assay," *Am. J. Hum. Genet.*, 1996, 58(6):1239-1246.
De Louvencourt et al., "Transformation of *Kluyveromyces lactis* by Killer Plasmid DNA," *J. Bacteriol.*, 1983, 154(2):737-742.
DeRisi et al., "Use of a cDNA microarray to analyse gene expression patterns in human cancer," *Nat. Genet.*, 1996, 14(4):457-460.
DeRisi et al., "Exploring the metabolic and genetic control of gene expression on a genomic scale," *Science*, 1997, 270:680-686.
Deuter and Müller, "Detection of APC Mutations in Stool DNA of Patients With Colorectal Cancer by HD-PCR," *Hum. Mutat.*, 1998, 11:84-89.
Dey, "Role of ancillary techniques in diagnosing and subclassifying non-Hodgkin's lymphomas on fine needle aspiration cytology," *Cytopathology*, 2006, 17:275-287.
Dijkema et al., "Cloning and expression of the chromosomal immune interferon gene of the rat," *EMBO J.*, 1985, 4:761-767.
Drmanac et al., "Accurate sequencing by hybridization for DNA diagnostics and individual genomics," *Nat. Biotech.*, 1998, 16:54-58.
Drmanac and Drmanac, "cDNA Screening by Array Hybridization," *Meth. Enzymol.*, 1999, 303:165-178.
Drmanac et al., "DNA Sequence Determination by Hybridization: A Strategy for Efficient Large-Scale Sequencing," *Science*, 1993, 260:1649-1652.
Duckworth et al., "Rapid synthesis of oligodeoxyribonucleotides VI. Efficient, mechanised synthesis of heptadecadeoxyribonucleotides by an improved solid phase phosphotriester route," *Nucl. Acids Res.*, 1981, 9:1691.
Edge et al., "Total synthesis of a human leukocyte interferon gene," *Nature*, 1981, 292:756-762.
Elsawa et al., "B-lymphocyte stimulator (BLyS) stimulates immunoglobulin production and malignant B-cell growth in Waldenström macroglobulinemia," *Blood*, 2006, 107:2882-2888.
Friesen and Miller, "The Regulation of Baculovirus Gene Expression," *Curr. Topics Microbiol. Immunol.*, 1986, 131:31-49.
Gaillardin et al., "Integrative transformation of the yeast *Yarrowia lipolytica*," *Curr. Genet.*, 1985, 10:49-58.
Ginot, "Oligonucleotide Micro-Arrays for Identification of Unknown Mutations: How Far from Reality?" *Human Mutation*, 1997, 10:1-10.
Gleeson et al., "Transformation of the Methylotrophic Yeast *Hansenula polymorpha*," *J. Gen. Microbiol.*, 1986, 132:3459-3465.
Goeddel et al., "Direct expression in *Escherichia coli* of a DNA sequence coding for human growth hormone," *Nature*, 1979, 281:544-548.
Goeddel et al., "Synthesis of human fibroblast interferon by *E. coli*," *Nucl. Acids Res.*, 1980, 8:4057-4074.
Gorman et al., "The Rous sarcoma virus long terminal repeat is a strong promoter when introduced into a variety of eukaryotic cells by DNA-mediated transfection," *Proc. Natl. Acad. Sci. USA*, 1982, 79:6777.
Gross et al., "TACI and BCMA are receptors for a TNF homologue implicated in B-cell autoimmune disease," *Nature*, 2000, 404:995-999.
Hacia et al., "Detection of heterozygous mutations in BRCA1 using high density oligonucleotide arrays and two-colour fluorescence analysis," *Nature Genetics*, 1996, 14:441-447.
Ham and Wallace, "Media and Growth Requirements," *Meth. Enzymol.*, 1979, 58:44-93.
Hani et al., "A missense mutation in hepatocyte nuclear factor-4 alpha, resulting in a reduced transactivation activity, in human late-onset non-insulin-dependent diabetes mellitus," *J. Clin. Invest.*, 1998, 101:521-526.
He et al., "Lymphoma B Cells Evade Apoptosis through the TNF Family Members BAFF/BLyS and April," *J. Immunol.*, 2004, 172:3268-3279.
Healey et al., "Fiberoptic DNA Sensor Array Capable of Detecting Point Mutations," *Anal. Biochem.*, 1997, 251:270-279.
Hinnen et al., "Transformation of yeast," *Proc. Natl. Acad. Sci. USA*, 1978, 75:1929-1933.
Hong, "Sequencing of large double-stranded DNA using the dideoxy sequencing technique," *Bioscience Reports*, 1982, 2:907-912.
Huard et al., "BAFF production by antigen-presenting cells provides T cell co-stimulation," *Int. Immunity*, 2004, 16:467.
Israel et al., "Clinical Pretreatment Risk Factors and Ga-67 Scintigraphy Early during Treatment for Prediction of Outcome of Patients with Aggressive Non-Hodgkin Lymphoma," *Cancer*, 2002, 94:873-878.
Ito et al., "Transformation of intact yeast cells treated with alkali cations," *J. Bacteriol.*, 1983,153:163-168.
Jiang et al., "Polymorphism and chromosomal mapping of the mouse gene for B-cell activating factor belonging to the tumor necrosis factor family (*Baff*) and association with the autoimmune phenotype," *Immunogenetics*, 2001, 53:810-813.
Kawasaki et al., "Analysis on the association of human BLYS (BAFF, TNFSF13B) polymorphisms with systemic lupus erythematosus and rheumatoid arthritis," *Gene Immun.*, 2002, 3:424-429.
Kelly and Hynes, "Transformation of *Aspergillus niger* by the *amdS* gene of *Aspergillus nidulans*," *EMBO J.*, 1985, 4(2):475-479.
Keown et al., "Methods for Introducing DNA into Mammalian Cells," *Meth. Enzymol.*, 1990, 185:527-537.
Kozal et al., "Extensive polymorphisms observed in HIV-1 clade B protease gene using high-density oligonucleotide arrays," *Nature Med.*, 1996, 2:753-759.
Krumbholz et al., "BAFF is produced by astrocytes and up-regulated in multiple sclerosis lesions and primary central nervous system lymphoma," *J. Exp. Med.*, 2005, 201:195.
Kunze et al., "Transformation of the industrially important yeasts *Candida maltosa* and *Pichia guilliermondii*," *J. Basic Microbiol.*, 1985, 25:141-144.
Kurtz et al., "Integrative transformation of *Candida albicans*, using a cloned *Candida* ADE2 gene," *Mol. Cell. Biol.*, 1986, 6:142.
Lebacq-Verheyden et al., "Posttranslational processing of endogenous and of baculovirus-expressed human gastrin-releasing peptide precursor," *Mol. Cell. Biol.*, 1988, 8:3129.
Lockhart et al., "Expression monitoring by hybridization to high-density oligonucleotide arrays," *Nat. Biotechnol.*, 1996, 14:1675-1680.
Luckow and Summers, "Trends in the Development of Baculovirus Expression Vectors," *Bio/Technology*, 1988, 6:47-55.
Maeda et al., "Production of human α-interferon in silkworm using a baculovirus vector," *Nature*, 1985, 315:592-594.
Mansfield et al., "Automation of Genetic Linkage Analysis Using Fluorescent Microsatellite Markers," *Genomics*, 1994, 24:225-233.
Marshall and Hodgson, "DNA chips: An array of possibilities," *Nat. Biotechnol.*, 1998, 16:27-31.
Martin et al., "Glycosylation and Processing of High Levels of Active Human Glucocerebrosidase in Invertebrate Cells Using a Baculovirus Expression Vector," *DNA*, 1988, 7(2):99-106.
Matsumoto et al., "Arthritis provoked by linked T and B cell recognition of a glycolytic enzyme," *Science*, 1999, 286:1732-1735.

McGraw, "Dideoxy DNA sequencing with end-labeled oligonucleotide primers," *Anal. Biochem.*, 1984, 143(2):298-303.
Mikhaeel et al., "FDG-PET after two to three cycles of chemotherapy predicts progression-free and overall survival in high grade non-Hodgkin's lymphoma," *Ann. Oncol.*, 2005, 16:1514-1523.
Miller, "Baculoviruses as Gene Expression Vectors," *Ann. Rev. Microbiol.*, 1988, 42:177-199.
Miller et al., "An Insect Baculovirus Host-Vector System for High-Level Expression of Foreign Genes," *Genetic Engineering*, 1986, 8:277-298.
Milosavljevic et al., "DNA sequence recognition by hybridization to short oligomers: Experimental verification of the method on the *E. coli* Genome," *Genomics*, 1996, 37:77-86.
Miyajima et al., "Use of the silkworm, *Bombyx mori*, and an insect baculovirus vector for high-level expression and secretion of biologically active mouse interleukin-3," *Gene*, 1987, 58:273-281.
Mukhopadhyay et al., "Identification and characterization of a novel cytokine, THANK, a TNF homologue that activates apoptosis, nuclear factor-kappa B, and c-Jun NH2-terminal kinase," *J. Biol. Chem.*, 1999, 274:15978-15981.
Moore et al., "BLyS: member of the tumor necrosis factor family and B lymphocyte stimulator," *Science*, 1999, 285(5425):260-263.
Mummidi et al., "Evolution of Human and Non-human Primate CC Chemokine Receptor 5 Gene and mRNA," *J. Biol. Chem.*, 2000, 275(25):18946-18961.
Nardelli et al., "Synthesis and release of B-lymphocyte stimulator from myeloid cells," *Blood*, 2001, 97:198-204.
Ng et al., "B Cell-Activating Factor Belonging to the TNF Family (BAFF)-R Is the Principal BAFF Receptor Facilitating BAFF Costimulation of Circulating T and B Cells," *J. Immunol.*, 2004; 173:807.
Novak et al., "Expression of BLyS and its receptors in B-cell non-Hodgkin lymphoma: Correlation with disease activity and patient outcome," *Blood*, 2004, 104:2247-2253.
Novak et al., "Aberrant expression of B-lymphocyte stimulator by B chronic lymphocytic leukemia cells: a mechanism for survival," *Blood*, 2002, 100(8):2973-2979.
Novak et al., "Expression of BCMA, TACI, and BAFF-R in multiple myeloma: a mechanism for growth and survival," *Blood*, 2004, 103:689-694.
Novak et al., "Elevated serum B-lymphocyte stimulator levels in patients with familial lymphoproliferative disorders," *J. Clin. Oncol.*, 2006, 24(6):983-987.
Novak et al., "Elevated BLyS levels in patients with familial and sporadic BCLL: Correlation with BLYS polymorphisms," *Blood*, 2004, 104(11):276A.
Novak et al., "Polymorphisms in the BLyS gene are associated with an increased risk of developing B-Cell non-Hodgkin lymphoma," *Blood*, 2007, 110(11):173A, abstract.
Pietu et al., "Novel gene transcripts preferentially expressed in human muscles revealed by quantitative hybridization of a high density cDNA array," *Genome Res.*, 1996, 6:492-503.
Ramsay, "DNA chips: State-of-the art," *Nature Biotech.*, 1998, 16:40-44.
Raval, "Qualitative and Quantitative Determination of mRNA," *J. Pharmacol. Toxicol. Meth.*, 1994, 32:125-127.
Riley et al., "A novel, rapid method for the isolation of terminal sequences from yeast artificial chromosome (YAC) clones," *Nucleic Acids Res.*, 1990, 18:2887-2890.
Roggenkamp et al., "Transformation of the methylotrophic yeast *Hansenula polymorpha* by autonomous replication and integration vectors," *Mol. Gen. Genet.*, 1986, 202:302-308.
Saiki et al., "Genetic analysis of amplified DNA with immobilized sequence-specific oligonucleotide probes," *Proc. Natl. Acad. Sci. USA*, 1989, 86:6230.
Saiki et al., "Analysis of enzymatically amplified β-globin and HLA-DQα DNA with allele-specific oligonucleotide probes," *Nature*, 1986, 324:163.
Sapolsky and Lipshutz, "Mapping Genomic Library Clones Using Oligonucleotide Arrays," *Genomics*, 1996, 33:445-456.
Scapini et al., "G-CSF—stimulated Neutrophils Are a Prominent Source of Functional BLyS," *J. Exp. Med.*, 2003, 297-302.
Schena et al., "Quantitative monitoring of gene expression patterns with complementary DNA microarray," *Science*, 1995, 270:467.
Schneider, "The role of April and BAFF in lymphocyte activation," *Curr. Op. Immunol.*, 2005, 17:282-289.
Schneider et al., "BAFF, a Novel Ligand of the Tumor Necrosis Factor Family, Stimulates B Cell Growth," *J. Exp. Med.*, 1999, 189:1747-1756.
Shalon et al., "A DNA Microarray System for Analyzing Complex DNA Samples Using Two-color Fluorescent Probe Hybridization," *Genome Res.*, 1996, 6:639.
Shoemaker et al., "Quantitative phenotypic analysis of yeast deletion mutants using a highly parallel molecular bar-coding strategy," *Nat. Genet.*, 1996, 14:450-456.
Shu et al., "TALL-1 is a novel member of the TNF family that is down-regulated by mitogens," *J. Leukoc. Biol.*, 1999, 65:680-683.
Siebenlist et al., "*E. coli* RNA polymerase interacts homologously with two different promoters," *Cell*, 1980, 20:269-281.
Smith et al., "Modification and secretion of human interleukin 2 produced in insect cells by a baculovirus expression vector," *Proc. Natl. Acad. Sci. USA*, 1985, 82:8404-8408.
Soares, "Identification and cloning of differentially expressed genes," *Curr. Opin. Biotechnol.*, 1997,8:542-546.
Stemmer et al., "Single-step assembly of a gene and entire plasmid from large numbers of oligodeoxyribonucleotides," *Gene*, 1995, 164:49-53.
Stemmer, "Rapid evolution of a protein in vitro by DNA shuffling," *Nature*, 1994, 370:389-391.
Stolz and Tuan, "Hybridization of Biotinylated Oligo(dT) for Eukaryotic mRNA Quantitation," *Mol. Biotechnol.*, 1996, 6:225-230.
Sutherland et al., "BAFF Augments Certain Th1-Associated Inflammatory Responses," *J. Immunol.*, 2005, 174:5537-5544.
Tilburn et al., "Transformation by integration in *Aspergillus nidulans*," *Gene*, 1983, 26:205-221.
Underhill et al., "A pre-Columbian Y chromosome-specific transition and its implications for human evolutionary history," *Proc. Natl. Acad. Sci. USA*, 1996, 93:196-200.
van den Berg et al., "*Kluyveromyces* as a Host for Heterologous Gene Expression: Expression and Secretion of Prochymosin," *Bio/Technology*, 1990, 8:135-139.
Vaughan and McCarthy, "A novel process for mutation detection using uracil DNA-glycosylase," *Nucl. Acids Res.*, 1998, 26:810-815.
Vlak et al., "Functional Studies on the p10 Gene of *Autographa californica* Nuclear Polyhedrosis Virus Using a Recombinant Expressing a p10-J-Galactosidase Fusion Gene," *J. Gen. Virol.*, 1988, 69:765-776.
Waldschmidt and Noelle, "Long Live the Mature B Cell—a BAF-Fling Mystery Resolved," *Science*, 2001, 293:2012-2013.
Wang et al., "Large-scale identification, mapping, and genotyping of single-nucleotide polymorphisms in the human genome," *Science*, 1998, 280:1077-1082.
Wodicka et al., "Genome-wide expression monitoring in *Saccharomyces cerevisiae*," *Nat. Biotech.*, 1997,15:1359-1367.
Wong and Senadheera, "Direct detection of multiple point mutations in mitochondrial DNA," *Clin. Chem.*, 1997, 43:1857-1861.
World Health Organization Classification of Neoplastic Diseases of the Hematopoietic and Lymphoid Tissue, 2001, Jaffe et al. (eds.).
Yelton et al., "Transformation of *Aspergillus nidulans* by using a trpC plasmid," *Proc. Natl. Acad. Sci.* (USA), 1984, 81:1470-1474
Yershov et al., "DNA analysis and diagnostics on oligonucleotide microchips," *Proc. Natl. Acad. Sci. USA*, 1996, 93:4913-4918.
Zhao et al., "High-density cDNA filter analysis: a novel approach for large-scale, quantitative analysis of gene expression," *Gene*, 1995, 156:207-213.
Ziegle et al., "Application of automated DNA sizing technology for genotyping microsatellite loci," *Genomics*, 1992, 14:1026-1031.
Authorized Officer Sabina Maretto, Invitation to Pay Additional Fees and, Where Applicable, Protest Fee, PCT/US2008/84854, mailed Mar. 23, 2009, 8 pages.
Authorized Officer Sabina Maretto, International Search Report/Written Opinion, PCT/US2008/84854, mailed Jun. 12, 2009, 22 pages.
Office Action, U.S. Appl. No. 11/555,559 mailed May 27, 2009, 14 pages.

\* cited by examiner

POLYMORPHISMS OF THE BLYS GENE AND USE IN DIAGNOSTIC METHODS

RELATED APPLICATIONS

This application claims the benefit of U.S. Provisional Application Ser. No. 60/991,509, filed Nov. 30, 2007, which is herein incorporated by reference.

STATEMENT AS TO FEDERALLY SPONSORED RESEARCH

This invention was made with government support under CA092104 and CA097274 awarded by the National Cancer Institute. The government has certain rights in the invention.

BACKGROUND OF THE INVENTION

B lymphocyte stimulator (BLyS) is a tumor necrosis factor (TNF) family member critical for maintenance of normal B cell development and homeostasis. It has been described by multiple names including BLyS (Moore et al. *Science* 1999; 285:260-263); BAFF (Schneider et al. *J Exp Med* 1999; 189: 1747-1756); THANK (Mukhopadhyay et al. *J Biol Chem* 1999; 274:15978-15981); and TALL-1 (Shu et al. *J Leukoc Biol* 1999; 65:680-683). This ligand binds to three receptors in the TNF family: transmembrane activator and CAML interactor (TACI), B cell maturation antigen (BCMA) and BAFF receptor (BAFF-R) (Gross et al. *Nature* 2000; 404: 995-999 and Thompson et al. *Science* 2001; 293:2012-2013). In normal animals, BLyS is expressed by monocytes, macrophages, dendritic cells, neutrophils, and radiation-resistant (non-myeloid) cells hypothesized to be stromal cells of lymphoid organs (reviewed in Schneider, *Curr Op Immunol* 2005; 17:282-289). BLyS production has been shown to be regulated by various cytokines including interferon gamma (IFN-γ), granulocyte and macrophage colony stimulating factor (GM-CSF) and interleukin 10 (IL-10) (Scapini et al. *J Exp Med* 2003; 297-302 and Nardelli et al. *Blood* 2001; 97:198-204).

Because overexpression of BLyS in transgenic animals resulted in autoimmune-like symptoms, reminiscent of systemic lupus erythematosus (SLE) and Sjörgens Syndrome (see Gross et al., supra.), investigation into BLyS levels in the clinic initially focused on autoimmune diseases. Genetic analysis of patients with SLE and rheumatoid arthritis (RA) discovered certain polymorphisms in the gene structure, although none of the polymorphisms could be associated in a statistically significant way with susceptibility to either disease (Kawasaki et al. *Gen & Immun* 2002; 3:424-429). However, one mutation (C→T at position −871) was shown to be associated with increased anti-Sm antibody and elevated monocyte BLyS levels.

Later work has focused on the role of BLyS in hematological malignancies. BLyS has been shown to be expressed in malignant B cells such as B chronic lymphocytic leukemia (B-CLL) cells Novak et al. *Blood* 2002; 100: 2973-2979), multiple myeloma (MM) (Novak et al. *Blood* 2004; 103:689-694), B-cell lymphoma (He et al. *J Immunol* 2004; 172: 3268-3279), and non-Hodgkin's lymphoma (HL) (Briones et al. *Exp Hematol* 2002; 30:135-141). For NHL, levels of BLyS and its receptors has been correlated with disease activity and patient outcome (Novak et al. *Blood* 2004; 104: 2247-2253). Overexpression of this ligand has also been demonstrated in patients with Waldenstrom's Macroglobulinema (WM), a further B cell malignancy (Elsawa et al., *Blood* 2006; 107: 2882-2888).

An additional area where BLys levels have been measured is in T cells, particularly in association with T cell related diseases, including T cell malignancies and autoimmune diseases with strong T cell association such as multiple sclerosis (Krumbholz et al. 2005; *J Exp Med* 201:195) and rheumatoid arthritis (Matsumoto et al. *Science* 1999; 286: 1732-1753). Several groups have examined the significant effect of BLyS on T cell stimulation (Ng et al. *J Immunol* 2004; 173: 807 and Huard et al. *Int Immunity* 2004; 16: 467). This observation was broadened to include Th1 and Th2 responses and T cell mediated inflammatory reactions (Sutherland et al. *J Immunol* 2005; 174: 5537-5544). Thus, it appears that BLyS may play a general role in hematological cancers whether originating from B cells or T cells.

There remains a need in the art for further identification of genetic polymorphisms of the BLyS gene or the sequences that control its expression that are statistically associated with hematological malignancies, such as B-cell malignancies. Such information is important for identifying individuals who have a propensity toward developing such hematological malignancies and for identifying new therapeutic agents for the treatment of these diseases. The present invention addresses this need by providing a polymorphism associated with both high BLyS levels and hematological cancers, and diagnostic tests determining the presence of this polymorphism.

SUMMARY OF THE INVENTION

The present invention provides isolated polypeptides comprising polymorphic nucleotide sequences of the BLyS gene identified as rs12583006, rs1224141, and rs12428930 (rs283296). Each of these single nucleotide polymorphisms (SNPs) occurs within intron sequences of the BLyS gene. The present invention provides a polypeptide comprising all three of these SNP sequences, in particular the major allele of each of these sequences. The polymorphic polypeptides of the present invention result in higher levels of BLyS polypeptide being produced thus resulting in BLyS activity. Other polymorphisms of the present invention may be located in the coding or non-coding portion of the gene. In some embodiments, the polymorphisms are associated with hematological malignancies. In some of these embodiments, the hematological malignancies are B cell malignancies, such as B-cell non-Hodgkin lymphoma (NHL). Isolated polymorphisms comprising one or more polymorphisms of the BLyS gene that are associated with hematological malignancies, as well as other tests characteristic of hematological malignancies as described fully below, are useful in diagnostic assays.

The present invention provides an isolated polynucleotide comprising a polymorphic nucleotide sequence from a B-lymphocyte stimulator (BLyS) gene. The polymorphism may be in a coding or non-coding portion of the gene. In some embodiments, polymorphisms are associated with a condition associated with BLyS activity. In particular, the SNPs identified as rs12583006, rs1224141, and rs12428930 (rs283296) are reported herein as statistically identified with conditions associated with BLyS activity, such as NHL. Even more particularly, the major allele of each of these SNPs are associated with an increased chance of B cell malignancies such as NHL, i.e., rs12583006 as a thymidine (T), rs1224141 as a thymidine (T), and rs12428930 (rs283296) as an adenine (A). Isolated polynucleotides comprising one or more polymorphisms in a BLyS gene such as these that are associated with a condition associated with BLyS activity are useful in diagnostic assays. Isolated polynucleotides comprising all three of these polymorphisms are particularly associated with an increased risk of B cell malignancies.

Accordingly, the invention further provides diagnostic assays for detecting the presence in a nucleic acid sample of a polymorphism in a BLyS gene that is associated with a condition associated with BLyS activity, such as hematological malignancy including B cell malignancies. Diagnostic assays are useful in predicting an individual's likelihood of developing a condition associated with BLyS activity, such as hematological malignancies. Thus, the invention further provides methods of detecting a propensity in an individual of developing a condition associated with BLyS activity, such as hematological malignancies. The invention further provides methods for genetically diagnosing in an individual a condition associated with BLyS activity, such as hematological malignancy. These methods generally involve detecting in a nucleic acid sample derived from an individual a BLyS polymorphism associated with a condition associated with BLyS activity. In some embodiments, diagnostic assays are conducted using a microarray comprising a BLyS polymorphic nucleic acid molecule.

Detection of BLyS polymorphisms associated with a condition associated with BLyS activity, such as hematological malignancy, allows selection of a treatment plan that is most likely to be effective in treating the condition. Thus, the invention further provides methods for treating an individual clinically diagnosed with a condition associated with BLyS activity, generally comprising detecting a BLyS polymorphism associated with a condition associated with BLyS activity, and selecting a treatment plan that is most effective for individuals clinically diagnosed as having a condition associated with BLyS activity. Detection of BLyS polymorphisms associated with a condition associated with BLyS activity also allows one to predict a patient's likelihood to respond to a specific drug treatment. Thus, the invention further provides methods of predicting a patient's likelihood to respond to a specific drug treatment for a condition associated with BLyS activity, such as hematological malignancy.

The invention further provides an array of nucleic acid molecules immobilized on a solid surface, where at least one of the nucleic acid molecules comprises a BLyS polymorphic nucleic acid molecule. The nucleic acid arrays of the invention allow rapid detection of hybridizing nucleic acid-molecules, in a nucleic acid sample from an individual, of a BLyS polymorphism associated with hematologial malignancy.

These and other aspects of the invention will become apparent to those persons skilled in the art upon reading the details of the invention as more fully described below.

BRIEF DESCRIPTION OF THE INVENTION

The present invention provides polymorphisms in the human BLyS gene that are associated with hematological malignancies, in particular B-cell malignancies, such as NHL, and methods of using nucleic acid molecules comprising the polymorphisms. The invention is based on the finding that polymorphisms in the intron region of the BLyS gene appear associated with the occurrence of NHL. Specifically, having a high risk allele at these three polymorphisms particularly increases the risk for diffuse large B-cell lymphoma and follicular lymphoma (grades I, II, or III) types of NHL. In each case, the high risk variant for the three identified SNPs was the major allele: for rs12583006 (T); rs1224141 (T); and re12428930 (A). This observation allows development of diagnostic assays to detect the presence of polymorphisms in an individual, which polymorphisms are associated with hematological malignancies, including B-cell malignancies, such as NHL, and therefore may predict the likelihood that an individual will develop a condition such as hematological malignancies, in particular, B-cell malignancies such as NHL, and provide insight as to the likely course of the disease upon its development. Although these polymorphisms are found within introns of the BLyS gene, it is known in the art that such sequences can alter the expression level of genes, see, for example, the increased expression driven by the CMV promoter when the sequences of intron A are present in a heterologous gene expression system (as described in the specifications of U.S. Pat. Nos. 5,591,639 and 5,658,759). Without being bound by theory, it is possible that the SNPs described herein are similarly associated with altered levels of transcription and/or translation of the BLyS protein as significantly higher levels of BLyS were measured in patients carrying such polymorphisms in their genome and thus these polymorphisms result in an increased risk in the development of B cell malignancies. This observation leads to the polynucleotides, polypeptides, and diagnostic tests of the present invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polymorphism includes a plurality of such polymorphisms, reference to "a nucleic acid molecule" includes a plurality of such nucleic acid molecules, and reference to "the method" includes reference to one or more methods, method steps, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein, the term "BLyS gene" is intended to generically refer to both the wild-type and variant forms of the sequence, unless specifically denoted otherwise. As it is commonly used in the art, the term "gene" is intended to refer to the genomic region encompassing 5' untranslated region(s) (UTR), exons, introns, and 3' UTR. Individual segments may be specifically referred to, e.g. promoter, coding region, etc. Combinations of such segments that provide for a complete BLyS protein may be referred to generically as a protein coding sequence. The nucleotide sequences of BLyS mRNA are publicly available through GenBank: Accession No. NM 052945 (human BLyS mRNA). Provided is the human cDNA sequence as SEQ ID NO: 1, the human protein sequence as SEQ ID NO:2. Also encompassed are its human variants disclosed as Accession Nos. 003808, 172087, 172088. Further, Accession No. 033622 (mouse BLyS mRNA) is contemplated. Provided is the mouse cDNA as SEQ ID NO:3, protein sequence as SEQ ID NO:4.

The term "polymorphism", as used herein, refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions. In particular, three polymorphisms of interest have been identified as rs12583006, rs1224141, and rs12428930 (rs283296) and can be viewed in the single nucleotide polymorphism section of the NCBI website and the BLyS sequences carrying the major alleles are disclosed as SEQ ID NO:5, SEQ ID NO:6, and SEQ ID NO:7, respectively in the present specification. It is noted that the major alleles of all three of these SNPs are those associated with higher risk of developing B cell malignancies, whereas the minor alleles are associated with lower risk of developing B cell malignancies.

As used herein, the term "polymorphic BLyS nucleic acid molecule" refers to a polynucleotide derived from a BLyS gene, which polynucleotide comprises one or more polymorphisms when compared to a reference BLyS polynucleotide sequence. A polymorphism present in a polymorphic BLyS nucleic acid molecule may be one that is associated with B-cell malignancies, such as NHL.

An "allele" in relation to single nucleotide polymorphisms is the presence of a particular nucleotide at a particular genomic location. Alleles can be classified as "high risk alleles" if the presence of a particular nucleotide at a specific location is associated with an increased risk of developing a particular disease. Alleles can also be classified as "low risk alleles" if the presence of a particular nucleotide at a specific location does not appear to be associated with an increased risk of developing a particular disease.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

In the broadest sense, as used herein, the terms "a condition associated with BLyS activity," and "a disease condition associated with BLyS activity," refer to a condition or disease which results, directly or indirectly, from altered BLyS activity. "Altered BLyS activity," as used herein, includes one or more of the following: (1) BLyS biological activity that is higher or lower than normal BLyS biological activity; (2) a level of BLyS mRNA in a cell that is higher or lower than the normal level of BLyS mRNA for that cell type; and (3) a level of BLyS polypeptide that is higher or lower than the normal level of BLyS polypeptide. A condition associated with BLyS activity is also a condition or disease which is symptomatic of altered BLyS activity. "Normal BLyS biological activity," "normal BLyS mRNA levels," and "normal BLyS polypeptide levels" refer to BLyS activity that is in the normal range for an individual of a given species, and which is not associated with, or give rise to, a disease condition. A condition associated with BLyS activity includes, but is not limited to, hematological malignancies. "Hematological malignancies" are those diseases generally having the properties of anaplasia, invasiveness, and metastasis where the invasive cell is derived from the blood or blood forming tissues, such as those classified in the World Health Organization Classification of Neoplastic Diseases of the Hematopoietic and Lymphoid Tissue (Jaffe et al. (Eds.) (2001). These diseases include, but are not limited to B-cell malignancies, T-cell malignancies, and natural killer (K) cell malignancies. Among the B-cell malignancies associated with increased BLyS activities are B-CLL (including familial), MM, B-cell lymphoma, and NHL. A representative type of a condition associated with increased BLyS activity is NHL.

Other B cell malignancies contemplated for the present invention are all variants of the following hematological malignancies: precursor B-cell lymphoblastic leukemia, B-cell prolymphocytic leukemia, immunocytoma, mantle cell lymphoma, follicular lymphoma, cutaneous follicular lymphoma, marginal zone B-cell lymphoma, hairy cell leukemia, diffuse large B-cell lymphoma, mediastinal large B-cell lymphoma, intravascular large B-cell lymphoma, Burkitt lymphoma, monoclonal gammopathy of undetermined significance, plasma cell myeloma variants beyond multiple myeloma such as Indolent myeloma and smoldering myeloma, plasmacytomas, heavy chain disease, immunoglobulin deposition diseases such as systemic light chain disease and primary amyloidosis. Among the T-cell and NK cell malignancies contemplated for the present invention are all variants of the following malignancies: precursor T-cell lymphoblastic leukemia, T-cell prolymphocytic leukemia, T-cell granular lymphocytic leukemia, aggressive NK cell leukemia, nasal and nasal-type NK/T cell lymphoma, mycosis fungoides and Sezary syndrome, angioimmunoblastic T-cell lymphoma, peripheral T-cell lymphoma unspecified, such as Lennert's, anaplastic large cell lymphoma, primary cutaneous CD-30 positive T-cell lymphoproliferative disorders, subcutaneous panniculitis-like T-cell lymphoma, intestinal T-cell lymphoma, and hepatosplenic gamma/delta T-cell lymphoma. Other hematological malignancies contemplated within the scope of the present invention include all variants of, but are not limited to, Hodgkin Lymphoma, immunodeficiency related-lymphoproliferative disorders, histiocytic/dendritic cell neoplasms and related disorders, acute leukemias and myelodysplastic syndromes, and chronic myeloproliferative disorders.

The terms "a propensity to develop a condition associated with BLyS activity," as used herein, refers to a statistically significant increase in the probability of developing measurable characteristics of a condition associated with BLyS activity in an individual having a particular genetic lesion(s) or polymorphism(s) compared with the probability in an individual lacking the genetic lesion or polymorphism.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

Examples of stringent conditions are hybridization and washing at 50° C. or higher and in 0.1×SSC (9 mM NaCl/0.9 mM sodium citrate).

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

where [$X^+$] is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a "recombinant host cell".

The term "binds specifically," in the context of antibody binding, refers to high avidity and/or high affinity binding of an antibody to a specific polypeptide i.e., epitope of a polymorphic BLyS polypeptide. Antibody binding to an epitope on a specific polymorphic BLyS polypeptide (also referred to herein as "a polymorphic BLyS epitope") is preferably stronger than binding of the same antibody to any other epitope, particularly those which may be present in molecules in association with, or in the same sample, as the specific polypeptide of interest, e.g., binds more strongly to a specific BLyS polymorphic epitope than to a different BLyS epitope so that by adjusting binding conditions the antibody binds almost exclusively to the specific BLyS polymorphic epitope and not to any other BLyS epitope, and not to any other BLyS polypeptide which does not comprise the polymorphic epitope. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a specific polymorphic BLyS polypeptide with a binding affinity of $10^7$ mole/l or more, preferably $10^8$ mole/liters or more are said to bind specifically to the specific BLyS polymorphic polypeptide. In general, an antibody with a binding affinity of $10^6$ mole/liters or less is not useful in that it will not bind an antigen at a detectable level using conventional methodology currently used.

The terms "detectably labeled antibody," "detectably labeled anti-polymorphic BLyS polypeptide," "detectably labeled anti-BLyS polymorphic epitope," or "detectably labeled anti-BLyS polymorphic polypeptide fragment" refer to an antibody (or antibody fragment which retains binding specificity for a polymorphic BLyS polypeptide or epitope), having an attached detectable label. The detectable label is normally attached by-chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

Isolated Polymorphic BLyS Nucleic Acid Molecules

The present invention provides isolated polynucleotides comprising one or more BLys polymorphic nucleic acid molecules. In some embodiments, the polymorphism is one associated with conditions associated with BLyS activity, such as hematological malignancies. The isolated polynucleotides are useful in a variety of diagnostic methods. Isolated polymorphic BLyS nucleic acid molecules of the invention can be used in one or more of the following methods: a) screening assays; b) predictive medicine (e.g., diagnostic assays, prognostics assays, monitoring clinical trials, and pharmacogenetics); and c) methods of treatment (e.g., therapeutic and prophylactic).

BLyS genes have been disclosed (see Moore et al.; Schneider et al.; Mukhopadhyay et al. and Shu et al. supra). The source of BLyS gene for use in the present invention can be any mammalian BLyS gene. In general, for diagnostic assays, the animal source of the BLyS gene will be the same species as the animal whose nucleic acid is being tested.

An isolated polymorphic BLyS nucleic acid molecule comprises one or more BLyS polymorphisms. Specifically, the following three polymorphisms: rs12583006, rs1224141, and rs12428930 (rs283296) have been found as associated with an increased risk of developing NHL. The sequences of these SNPs are reported within the BLyS genomic sequences labeled as SEQ ID NO:5, SEQ ID NO:6, and SEQ ID NO:7, respectively, in the present specification. It should be noted that the high risk allele for these SNPs in each case was the major allele. Specifically rs1258006 is T, rs1224141 is T, and rs12428930 (rs283296) is A. Highest risk for B cell malignancy is found for individuals which carry the major allele in all three of these polymorphisms, whereas the lowest risk is found for those individuals who have the less common allele at all three SNP sites.

In some embodiments, the polymorphic BLyS sequence can comprises one or more additional polymorphisms: (1) a G→A variation at or about nucleotide −1283 relative to the BLyS gene transcription start site; (2) a C→T variation at or about nucleotide −871 relative to the BLyS gene transcription start site; (3) a T→C variation at or about nucleotide −514 relative to the BLyS gene transcription start site; (4) a G→C variation at or about nucleotide −353 relative to the BLyS gene transcription start site; (5) a C→G variation at or about nucleotide 45 (within intron 1 of the BLyS gene) and (6) a G→A variation at or about nucleotide 313 (causing a Ala105Thr change in the protein sequence). The exact position of the aforementioned variants may vary from individual to individual or from species to species, e.g., by from 1 to about 10 base pairs. Further polymorphisms include those described by Jiang et al. *Immunogen* 2001; 53: 810-814.

For some uses, e.g., in screening assays, BLyS polymorphic nucleic acid molecules will be of at least about 15 nucleotides (nt), at least about 18 nt, at least about 20 nt, or at least about 25 nt in length, and often at least about 50 nt. Such small DNA fragments are useful as primers for polymerase chain reaction (PCR), hybridization screening, etc. Larger polynucleotide fragments, e.g., at least about 50 nt, at least about 100 nt, at least about 200 nt, at least about 300 nt, at least about 500 nt, at least about 1000 nt, at least about 1500 nt, up to the entire coding region, or up to the entire coding region plus up to about 1000 nt 5' and/or up to about 1000 nt 3' flanking sequences from a BLyS gene, are useful for production of the encoded polypeptide, promoter motifs, etc. For use in amplification reactions, such as PCR, a pair of primers will be used. The exact composition of primer sequences is not critical to the invention, but for most applications the primers will hybridize to the subject sequence under stringent conditions, as known in the art.

When used as a probe, an isolated polymorphic BLyS nucleic acid molecule may comprise non-BLyS nucleotide sequences, as long as the additional non-BLyS nucleotide sequences do not interfere with the detection assay. A probe may comprise an isolated polymorphic BLyS sequence, and any number of non-BLyS nucleotide sequences, e.g., from about 1 bp to about 1 kb or more.

For screening purposes, hybridization probes of the polymorphic sequences may be used where both forms are present, either in separate reactions, spatially separated on a solid phase matrix, or labeled such that they can be distinguished from each other. Assays (described below) may utilize nucleic acids that hybridize to one or more of the described polymorphisms.

Isolated polymorphic BLyS nucleic acid molecules of the invention may be coupled (e.g., chemically conjugated), directly or indirectly (e.g., through a linker molecule) to a solid substrate. Solid substrates may be any known in the art including, but not limited to, beads, e.g., polystyrene beads; chips, e.g., glass, SiO$_2$, and the like; plastic surfaces, e.g., polystyrene, polycarbonate plastic multi-well plates; and the like.

Isolated polymorphic BLyS nucleic acid molecules can be obtained by chemical or biochemical synthesis, by recombinant DNA techniques, or by isolating the nucleic acids from a biological source, or a combination of any of the foregoing. For example, the nucleic acid may be synthesized using solid phase synthesis techniques, as are known in the art. Oligonucleotide synthesis is also described in Edge et al. (1981) *Nature* 292:756; Duckworth et al. (1981) *Nucleic Acids Res.* 9:1691 and Beaucage and Caruthers (1981) *Tet. Letters* 22:1859. Following preparation of the nucleic acid, the nucleic acid is then ligated to other members of the expression system to produce an expression cassette or system comprising a nucleic acid encoding the subject product in operational combination with transcriptional initiation and termination regions, which provide for expression of the nucleic acid into the subject polypeptide products under suitable conditions.

Additional BLyS gene polymorphisms may be identified using any of a variety of methods known in the art, including, but not limited to SSCP, denaturing HPLC, and sequencing. Example 3 provides a description of how BLyS polymorphisms were identified using single strand conformation polymorphism (SSCP) analysis and denaturing HPLC analysis. SSCP may be used to identify additional BLyS gene polymorphisms. In general, PCR primers and restriction enzymes are chosen so as to generate products in a size range of from about 25 bp to about 500 bp, or from about 100 bp to about 250 bp, or any intermediate or overlapping range therein.

Polymorphic BLyS Polypeptides

The present invention provides isolated polymorphic BLyS polypeptides. Isolated polymorphic BLyS polypeptides are useful in assays to screen for agents that modify a biological activity of a BLyS polypeptide.

The term "polymorphic BLyS polypeptide" encompasses an amino acid sequence encoded by an open reading frame (ORF) of a known BLyS polynucleotide, including the full-length native polypeptide and fragments thereof, particularly biologically active fragments and/or fragments corresponding to functional domains, e.g. a region or domain having biological activity, etc.; antigenic fragments thereof, and including fusions of the subject polypeptides to other proteins or parts thereof. The amino acid sequences of BLyS polypeptides have been disclosed. See e.g. Moore et al., supra. A polymorphism in a BLyS polypeptide is generally defined relative to a reference sequence.

As used herein, "polymorphic BLyS polypeptide" refers to an amino acid sequence of a recombinant or non-recombinant polypeptide having an amino acid sequence of i) a native polymorphic BLyS polypeptide, ii) a fragment of a polymorphic BLyS polypeptide, iii) polypeptide analogs of a polymorphic BLyS polypeptide, iv) variants of a polymorphic BLyS polypeptide; v) an immunologically active fragment of a polymorphic BLyS polypeptide; and vi) fusion proteins comprising a polymorphic BLyS polypeptide. Polymorphic BLyS polypeptides of the invention can be obtained from a biological sample, or from any source whether natural, synthetic, semi-synthetic or recombinant.

The term "polymorphic BLyS polypeptide" encompasses a polypeptide comprising from at least about 5 amino acids, at least about 10 amino acids, at least about 15 amino acids, at least about 25 amino acids, at least about 50 amino acids, at least about 75 amino acids, at least about 100 amino acids, at least about 200 amino acids, at least about 300 amino acids, at least about 400 amino acids, or up to the entire polypeptide of a polymorphic BLyS polypeptide. In some embodiments, a polymorphic BLyS polypeptide exhibits biological activity, e.g., the polypeptide causes proliferation of B-cells and production of immunoglobulin in an in vitro assay. Other assays for BLyS biological activity are known in the art and can be used to determine whether a polymorphic BLyS polypeptide exhibits biological activity and, if desired, to quantitate BLyS biological activity. BLyS biological assays are described in various publications, e.g., Moore et al., supra.

Polymorphic BLyS polypeptides of the invention may be part of a fusion protein. Suitable fusion partners (e.g., a non-BLyS polypeptide, or "heterologous polypeptide") include, but are not limited to, a heterologous polypeptide that provides for immunological recognition, e.g., an epitope tag; a heterologous polypeptide that provides for a detectable signal, e.g., a green fluorescent protein (GFP), β-galactosidase, and the like; a heterologous polypeptide that provides for a catalytic function; and a heterologous polypeptide that facilitates entry into a cell. The fusion partner can be coupled in-frame to the N-terminus, the C-terminus, or both of the polymorphic BLyS polypeptide, using standard methods for synthesis of polypeptides, or using recombinant methods.

Polymorphic BLyS polypeptides of the invention can be obtained by any known method, or a combination of such methods, including isolation from natural sources; production by chemical synthesis; and production by standard recombinant techniques.

Polymorphic BLyS polypeptides can be isolated from a biological source, using affinity chromatography, e.g., using antibodies specific for a BLyS polypeptide are immobilized on a solid support. The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, CHO cells, HEK293 cells, and the like, may be used as the expression host cells. In some situations, it is desirable to express the gene in eukaryotic cells, where the protein will benefit from native folding and post-translational modifications. The polypeptide can then be isolated from cell culture supernatant or from cell lysates using affinity chromatography methods or anion exchange/size exclusion chromatography methods, as described above.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique.

Vectors and Host Cells Comprising the Polynucleotides of the Invention

The invention further provides recombinant vectors and host cells comprising polynucleotides of the invention. In general, recombinant vectors and host cells of the invention are isolated; however, a host cell comprising a polynucleotide of the invention may be part of a genetically modified animal.

Recombinant vectors. The present invention further provides recombinant vectors ("constructs") comprising a polynucleotide of the invention. Recombinant vectors include vectors used for propagation of a polynucleotide of the invention, and expression vectors. Vectors useful for introduction of the polynucleotide include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, at least about 25 amino acids, at least about 45 amino acids, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high copy-number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electroporation, fusion, transfection, infection with viral vectors, biolistics, etc.

Genetically Modified Cells. The present invention further provides host cells, which may be isolated host cells, comprising polymorphic BLyS nucleic acid molecules of the invention. Suitable host cells include prokaryotes such as *E. coli, B. subtilis*, eukaryotes, including insect cells in combination with baculovirus vectors, yeast cells, such as *Saccharomyces cerevisiae*, or cells of a higher organism such as vertebrates, including amphibians (e.g., *Xenopus laevis* oocytes), and mammals, particularly humans, e.g. COS cells, CHO cells, HEK293 cells, and the like, may be used as the host cells. Host cells can be used for the purposes of propagating a polymorphic BLyS nucleic acid molecule, for production of a polymorphic BLyS polypeptide, or in cell-based methods for identifying agents which modulate a level of BLyS mRNA and/or protein and/or biological activity in a cell.

Primary or cloned cells and cell lines may be modified by the introduction of vectors comprising a BLyS gene polymorphism(s). The isolated polymorphic BLyS nucleic acid molecule may comprise one or more variant sequences, e.g., a haplotype of commonly occurring combinations. In one embodiment of the invention, a panel of two or more genetically modified cell lines, each cell line comprising a BLyS polymorphism, are provided for substrate and/or expression assays. The panel may further comprise cells genetically modified with other genetic sequences, including polymorphisms, particularly other sequences of interest for pharmacogenetic screening, e.g. other genes/gene mutations associated with hematologic malignancies, a number of which are known in the art.

Transgenic animals. The subject nucleic acids can be used to generate genetically modified non-human animals or site specific gene modifications in cell lines. The term "transgenic" is intended to encompass genetically modified animals having a deletion or other knock-out of BLyS gene activity, having an exogenous BLyS gene that is stably transmitted in the host cells, or having an exogenous BLyS promoter operably linked to a reporter gene. Transgenic animals may be made through homologous recombination, where the BLyS locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

DNA constructs for homologous recombination will comprise at least a portion of a polymorphic BLyS nucleic acid molecule, and will include regions of homology to the target locus. Conveniently, markers for positive and negative selection are included. Methods for generating cells having targeted gene modifications through homologous recombination are known in the-art. For various techniques for transfecting mammalian cells, see Known et al. (1990) *Methods in Enzymology* 185:527-537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from. 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the BLyS gene and males and females having the modification are mated to produce homozygous progeny. The transgenic animals may be any non-human mammal, such as laboratory animals, domestic animals, etc. The transgenic animals may be used to determine the effect of a candidate drug on triglyceride synthesis in an in vivo environment.

Preparation of Polymorphic BLyS Polypeptides

In addition to the plurality of uses described in greater detail in following sections, the subject nucleic acid compositions find use in the preparation of all or a portion of the polymorphic BLyS polypeptides, as described above. The subject polynucleotides (including cDNA or the full-length gene) is used to express a partial or complete gene product. Constructs comprising the subject polynucleotides can be generated synthetically. Alternatively, single-step assembly of a gene and entire plasmid from large numbers of oligodeoxyribonucleotides is described by, e.g., Stemmer et al., *Gene (Amsterdam)* (1995) 164(1):49-53. In this method, assembly PCR (the synthesis of long DNA sequences from large numbers of oligodeoxyribonucleotides (oligos)) is described. The method is derived from DNA shuffling (Stemmer, *Nature* (1994) 370:389-391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, an polymorphic BLyS polypeptide-encoding polynucleotide is linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the BLyS gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Polymorphic BLyS polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, HEK 293, CHO, *Xenopus* Oocytes, etc., may be used as the expression host cells. In some situations, it is desirable to express a polymorphic BLyS nucleic acid molecule in eukaryotic cells, where the polymorphic BLyS protein will benefit from native folding and post-translational modifications. Small peptides can also be synthesized in the laboratory. Polypeptides that are subsets of the complete BLyS sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci. (USA)* (1983) 80:21-25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990)8:135; Kunze et al., *J. Basic Microbiol* (1985)25: 141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci. (USA)* (1984) 81:1470-1474; Kelly and Hynes, *EMBO J.* (1985) 4:475-479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409;

Maeda et al., *Nature* (1985) 315:592-594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated-in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject polymorphic BLyS proteins without manipulation of the encoding nucleic acid itself, but instead through integration of a regulatory sequence into the genome of cell that already includes a gene encoding the desired protein, as described in the above incorporated patent documents.

Antibodies Specific for Polymorphic BLyS Polypeptides

The invention further provides antibodies, particularly isolated antibodies, that are specific for polymorphic BLyS polypeptides of the invention. It should be noted that mutations within the protein sequence (unlike rs12583006, rs1224141, and rs12428930 (rs283296)) are generally believed required for antibodies specific to the altered protein sequence to be produced. The antibodies of the invention are useful in a variety of diagnostic assays, as described in further detail below. For example, an antibody of the invention can be used to detect a polymorphic BLyS polypeptide in a biological sample.

Isolated polymorphic BLyS polypeptides of the invention are useful for the production of antibodies, where short fragments provide for antibodies specific for the particular polypeptide, and larger fragments or the entire protein allow for the production of antibodies over the surface of the polypeptide. Accordingly, the invention provides isolated antibodies which specifically bind a polymorphic BLyS polypeptide, or antigenic fragment thereof. Antibodies may be raised to the wild-type or variant forms. Antibodies may be raised to isolated peptides corresponding to these domains, or to the native protein. Antibodies may be raised to polypeptides and/or peptide fragments of polymorphic BLyS from any mammalian species.

Particularly useful are antibodies that distinguish between or among BLyS polymorphic polypeptides. Antibodies may be generated that specifically recognize a BLyS polypeptide comprising one or more specific polymorphisms. Generation of such antibodies, and determination of their specificity relative to other BLyS polypeptides, is readily accomplished by those skilled in the art using conventional methods and assays. As one non-limiting example, an enzyme-linked immunosorbent assay (ELISA) can be used to determine the specificity of a given monoclonal antibody for a particular polymorphic BLyS polypeptide.

The polymorphic BLyS polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, fusion proteins comprising such antibody fragments, detectably labeled antibodies, and chimeric antibodies. "Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a polymorphic BLyS polypeptide.

Antibodies are prepared in accordance with conventional ways, where the expressed is polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. Coli*, and the heavy and light chains mixed to further enhance the affinity of the antibody. Alternatives to in vivo immunization as a method of raising antibodies include binding to phage display libraries, usually in conjunction with in vitro affinity maturation.

Antibodies may be attached, directly or indirectly (e.g., via a linker molecule) to a solid support for use in a diagnostic assay to determine and/or measure the presence of a polymorphic BLyS polypeptide in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an ELISA or radioimmunoassay (RIA), and the like); sheets, e.g., nylon, nitrocellulose, and the like; and chips, e.g., $SiO_2$ chips such as those used in microarrays. Accordingly, the invention further provides assay devices comprising antibodies attached to a solid support.

A single antibody or a battery of different antibodies can then be used to create an assay device. Such an assay device can be prepared using conventional technology known to those skilled in the art. The antibody can be purified and isolated using known techniques and bound to a support surface using known procedures. The resulting surface having antibody bound thereon can be used to assay a test sample, e.g., a biological sample, in vitro to determine if the sample contains one or more types of BLyS polymorphic polypeptides. For example, antibodies which bind only to a specific BLyS polymorphic epitope can be attached to the surface of a material. Alternatively, a plurality of specific antibodies, which may be arranged in an array, wherein antibodies specific for two or more different BLyS polymorphic epitopes are attached to the solid support, can be used. A test sample is brought into contact with the antibodies bound to the surface of material. Specific binding can be detected using any known method. If specific binding is not detected, it can be deduced that the sample does not contain the specific BLyS polymorphic epitope. As one non-limiting example of how specific binding can be detected, once the test sample has been contacted with the antibodies bound to the solid support, a second, detectably-labeled antibody can be added, which recognizes a BLyS epitope distinct from the epitope recognized by the solid support-bound antibody.

A variety of other reagents may be included in the assays to detect BLyS polymorphic polypeptides described herein. These include reagents such as salts, neutral proteins, e.g. albumin, detergents, etc., that are used to facilitate optimal protein-protein binding, and/or reduce non-specific or background interactions. Reagents that improve the efficiency of the assay, such as protease inhibitors, anti-microbial agents, etc. may be used. The components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient.

Compositions

The present invention further provides compositions, including pharmaceutical compositions, comprising the polypeptides, polynucleotides, antibodies, recombinant vectors, and host cells of the invention. These compositions may include a buffer, which is selected according to the desired use of the polypeptide, antibody, polynucleotide, recombinant vector, or host cell, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Diagnostic Assays

Isolated BLyS polymorphic nucleic acid molecules of the invention are useful in diagnostic assays. The present invention provides diagnostic methods for detecting, in a nucleic acid sample from an individual, a BLyS polymorphism associated with a condition associated with BLyS activity. The detection methods are useful in methods for identifying individuals predisposed to developing a condition associated with BLyS activity, as well as in methods for genetically diagnosing a condition associated with BLyS activity.

The invention further provides methods for detecting the presence of and/or a level of BLyS mRNA in a biological sample; and methods for detecting the presence of and/or a level of polymorphic BLyS polypeptide in a biological sample.

Thus, in some embodiments, a method is provided for detecting, in a polynucleotide sample derived from an individual, the presence of BLyS polymorphism associated with a disorder associated with BLyS activity in an individual, which method comprises analyzing a polynucleotide sample from an individual for the presence of a nucleotide sequence polymorphism in a BLyS gene, wherein the nucleotide sequence polymorphism is associated with a condition relating to abnormal fat storage.

In other embodiments, a method is provide for detecting a level of BLyS mRNA in a biological sample derived from an individual, comprising analyzing a polynucleotide sample from an individual for the level of BLyS polypeptide-encoding mRNA. The level of BLyS mRNA may be associated with a condition relating to BLyS activity.

In other embodiments, a method is provided for detecting a propensity of an individual to develop a condition associated with BLyS activity, comprising analyzing a polynucleotide sample derived from the individual for the presence of a polymorphism in a BLyS gene, wherein said BLyS-gene polymorphism is associated with a condition associated with BLyS activity.

In other embodiments, a method is provided for genetically diagnosing a condition associated with BLyS activity, comprising analyzing a polynucleotide sample from said individual for the presence of a polymorphism in a BLyS gene, wherein said BLyS gene polymorphism is associated with a condition associated with BLyS activity.

In still other embodiments, a method is provided for detecting the presence of and/or the level of a polymorphic BLyS polypeptide in a biological sample, such as a genomic sequence sample. In further embodiments, a method is provided for detecting the presence of and/or the level of a biological activity of a polymorphic BLyS polypeptide in a biological sample.

Polynucleotide samples derived from (e.g., obtained from) an individual are obtained from a biological sample taken from the individual. Any biological sample that comprises a polynucleotide from the individual is suitable for use in the methods of the invention. The biological sample may be processed so as to isolate the polynucleotide. Alternatively, whole cells or other biological samples may be used without isolation of the polynucleotides contained therein. Detection of a BLyS polymorphism that is associated with a disorder associated with BLyS activity in a polynucleotide sample derived from an individual can be accomplished by any means known in the art, including, but not limited to, amplification of a sequence with specific primers; determination of the nucleotide sequence of the polynucleotide sample; hybridization analysis; single strand conformational polymorphism analysis; denaturing gradient gel electrophoresis; mismatch cleavage detection; and the like. Detection of a BLyS polymorphism that is associated with a condition associated with BLyS activity can also be accomplished by detecting an alteration in the level of a mRNA transcript of a BLyS gene; aberrant modification of a BLyS gene, e.g., an aberrant methylation pattern; the presence of a non-wild-type splicing pattern of BLyS mRNA; an alteration in the level of BLyS polypeptide; and/or an alteration in BLyS polypeptide biological activity.

Detection of a BLyS polymorphism by analyzing a polynucleotide sample can be conducted in a number of ways. A test nucleic acid sample can-be amplified with primers which amplify a sequence region known to comprise a BLyS polymorphism(s). Non-limiting examples of such sequences are provided in Example 1. Genomic DNA or mRNA can be used directly. Alternatively, the region of interest can be cloned into a suitable vector and grown in sufficient quantity for analysis. The nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfand, and Sninsky, eds., Academic Press. Once the region comprising a BLyS polymorphism has been amplified, the BLyS polymorphism can be detected in the PCR product by nucleotide sequencing, by SSCP analysis, or any other method known in the art. In performing SSCP analysis, the PCR product may be digested with a restriction endonuclease that recognizes a sequence within the PCR product generated by using as a template a reference BLyS sequence, but does not recognize a corresponding PCR product generated by using as a template a variant BLyS sequence by virtue of the fact that the variant sequence no longer contains a recognition site for the restriction endonuclease.

PCR may also be used to determine whether a polymorphism is present by using a primer that is specific for the polymorphism. Such methods may comprise the steps of collecting from an individual a biological sample comprising the individual's genetic material as template, optionally isolating template nucleic acid (genomic DNA, mRNA, or both) from the biological sample, contacting the template nucleic acid sample with one or more primers that specifically hybridize with a BLyS polymorphic nucleic acid molecule under conditions such that hybridization and amplification of the template nucleic acid molecules in the sample occurs, and detecting the presence, absence, and/or relative amount of an amplification product and comparing tie length to a control sample. Observation of an amplification product of the expected size is an indication that the BLyS polymorphism contained within the BLyS polymorphic primer is present in the test nucleic acid sample. Parameters such as hybridization conditions, BLyS polymorphic primer length, and position of the polymorphism within the BLyS polymorphic primer may be chosen such that hybridization will not occur unless a polymorphism present in the primer(s) is also present in the sample nucleic acid. Those of ordinary skill in the art are well aware of how to select and vary such parameters. See, e.g., Saiki et al. (1986) *Nature* 324:163; and Saiki et al (1989) *Proc. Natl. Acad. Sci. USA* 86:6230. As one non-limiting example, a PCR primer comprising the T78C variation described in Example 1 may be used.

Alternatively, various methods are known in the art that utilize oligonucleotide ligation as a means of detecting polymorphisms. See, e.g., Riley et al. (1990) *Nucleic Acids Res.* 18:2887-2890; and Delahunty et al. (1996) *Am. J Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid may be sequenced by a dideoxy chain termination method or other well-known methods. Genomic DNA or mRNA may be used directly. If mRNA is used, a cDNA copy may first be made. If desired, the sample nucleic acid can be amplified using a PCR. A variety of sequencing reactions known in the art can be used to directly sequence the BLyS gene, or a portion thereof in which a specific polymorphism is known to occur, and detect polymorphisms by comparing the sequence of the sample nucleic acid with a reference polynucleotide that contains a BLyS polymorphism. Any of a variety of automated sequencing procedures can be used. See, e.g., WO 94/16101; Cohen et al. (1996) *Adv. Chromatography* 36:127-162.

Hybridization with the variant sequence may also be used to determine the presence of a BLyS polymorphism. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Identification of a polymorphism in a nucleic acid sample can be performed by hybridizing a sample and control nucleic acids to high density arrays containing hundreds or thousands of oligonucleotide probes. Cronin et al. (1996) *Human Mutation* 7:244-255; and Kozal et al. (1996) *Nature Med.* 2:753-759.

Single strand conformational polymorphism (SSCP) analysis; denaturing gradient gel electrophoresis (DGGE); mismatch cleavage detection; and heteroduplex analysis in gel matrices can also be used to detect polymorphisms. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

A number of methods are available for determining the expression level of a polymorphic BLyS nucleic acid molecule, e.g., a polymorphic BLyS mRNA, or polymorphic BLyS polypeptide in a particular sample. Diagnosis may be performed by a number of methods to determine the absence or presence or altered amounts of normal or abnormal BLyS mRNA in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled ith radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. The presence and/or the level of a polymorphic BLyS polypeptide may also be detected and/or quantitated in any way known to one of ordinary skill.

In addition, a test can include measurements of the expression of BLyS mRNA. Biochemical studies may be performed to determine whether a sequence polymorphism in a BLyS coding region or control regions is associated with disease. Disease associated polymorphisms may include deletion or truncation of the gene, mutations that alter expression level, that affect the activity of the protein, etc.

Changes in the promoter or enhancer sequence that may affect expression levels of BLyS can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Screening for mutations in a polymorphic BLyS polypeptide may be based on the functional or antigenic characteristics of the protein. Protein truncation assays are useful in detecting deletions that may affect the biological activity of the protein. Various immunoassays designed to detect polymorphisms in polymorphic BLyS polypeptides may be used in screening. Where many diverse genetic mutations lead to a particular disease phenotype, functional protein assays have proven to be effective screening tools. The activity of the encoded a polymorphic BLyS polypeptide may be determined by comparison with a reference BLyS polypeptide lacking a specific polymorphism.

Diagnostic methods of the subject invention in which the level of BLyS gene expression is of interest will typically involve comparison of the BLyS nucleic acid abundance of a sample of interest with that of a control value to determine any relative differences, where the difference may be measured qualitatively and/or quantitatively, which differences are then related to the presence or absence of an abnormal BLyS gene expression pattern. A variety of different methods for determine the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Additional tests that have been associated with NHL disease severity or progression can be combined with the polymorphism test described above to render a full diagnosis or outlook result. One test that can be combined with the polymorphism test is a measurement of tumor cell or serum BLyS levels (Novak et al. Blood 2002, supra). Among other tests that can be combined are, positron emission tomography with 2-[18F]fluororo-2-deoxy-D-glucose (FDG-PET) (see Mikhaeel et al., Ann. Oncol. 2005 16:1514-23); fine needle cytology (on its own or combined with immunocytochemistry, flow cytometry, Southern blot analysis, polymerase chain reaction and fluorescent in situ hybridization (FISH)) (see Dey, Cytopathology, 2006 17:275-87); and Ga-67 scintigraphy (see Israel et al., Cancer, 2002 94:873-878.)

Monitoring Effects of Drug Treatment

Monitoring the influence of agents (e.g., drugs, compounds) on the expression or activity of a BLyS protein (e.g., modulation of transcriptional activation) can be applied not only in basic drug screening, but also in clinical trials. For example, the effectiveness of an agent determined by a screening assay as described herein to increase BLyS gene expression, protein levels, or upregulate BLyS activity, can be monitored in clinical trials of subjects exhibiting decreased BLyS gene expression, protein levels, or down-regulated BLyS activity. Alternatively, the effectiveness of an agent determined by a screening assay to decrease BLyS gene expression, protein levels, or downregulate BLyS activity, can be monitored in clinical trials of subjects exhibiting increased BLyS gene expression, protein levels, or upregulated BLyS activity. In such clinical trials, the expression or activity of a BLyS gene, and preferably, other genes that have been implicated in, for example, a disorder associated with BLyS activity can be used as a "read out" or markers of the phenotype of a particular cell.

For example, and not by way of limitation, genes, including BLyS, that are modulated in cells by treatment with an agent (e.g., compound, drug or small molecule) which modulates BLyS activity (e.g., identified in a screening assay as described herein) can be identified. Thus, to study the effect of agents on fat storage disorders, for example, in a clinical trial, cells can be isolated and RNA prepared and analyzed for the levels of expression of BLyS and other genes implicated in a disorder associated with BLyS activity. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of BLyS or other genes. In this way, the gene expression pattern can serve as a marker, indicative of the physiological response of the cells to the agent. Accordingly, this response state may be determined before, and at various points during treatment of the individual with the agent.

In some embodiments, the present invention provides a method for monitoring the effectiveness of treatment of a subject with an agent (e.g., an agonist, antagonist, peptidomimetic, protein, peptide, nucleic acid, small molecule, or other drug that modifies a BLyS activity) comprising the steps of (i) obtaining a pre-administration sample from a subject prior to administration of the agent; (ii) detecting the level of expression of a BLyS protein, mRNA, or genomic DNA in the pre-administration sample; (iii) obtaining one or more post-administration samples from the subject, (iv) detecting the level of expression or activity of the BLyS protein, mRNA, or genomic DNA in the post-administration samples; (v) comparing the level of expression or activity of the BLyS protein, mRNA, or genomic DNA in the pre-administration sample with the BLyS protein, mRNA, or genomic DNA in the post administration sample or samples; and (vi) altering the administration of the agent to the subject accordingly. For example, increased administration of the agent may be desirable to increase the expression or activity of BLyS to higher levels than detected, i.e., to increase the effectiveness of the agent. Alternatively, decreased administration of the agent may be desirable to decrease expression or activity of BLyS to lower levels than detected, i.e. to decrease the effectiveness of the agent. According to such an embodiment, BLyS expression or activity may be used as an indicator of the effectiveness of an agent, even in the absence of an observable phenotypic response.

Linkage Analysis: Diagnostic screening may be performed for polymorphisms that are genetically linked to a phenotypic variant in BLyS activity or expression, particularly through the use of microsatellite markers or single nucleotide polymorphisms (SNP). The microsatellite or SNP polymorphism itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium.

Linkage analysis may be performed alone, or in combination with direct detection of phenotypically evident polymorphisms. The use of microsatellite markers for genotyping is well documented. For examples, see Mansfield et al. (1994) *Genomics* 24:225-233; and Ziegle et al. (1992) *Genomics* 14:1026-10331. The use of SNPs for genotyping is illustrated in Underhill et al. (1996) *Proc. Natl. Acad. Sci. USA* 93:196-200.

Genetic linkage maps show the relative locations of specific DNA markers along a chromosome. Any inherited physical or molecular characteristic that differs among individuals and is easily detectable in the laboratory is a potential genetic marker. DNA sequence polymorphisms are useful markers because they are plentiful and easy to characterize precisely. Many such polymorphisms are located in non-coding regions and do not affect the phenotype of the organism, yet they are detectable at the DNA level and can be used as markers. Examples include restriction fragment length polymorphisms (RFLPs), which reflect sequence variations in DNA sites or differences in the length of the product, which can be cleaved by DNA restriction enzymes, microsatellite markers, which are short repeated sequences that vary in the number of repeated units, single nucleotide polymorphisms (SNPs), and the like.

The "linkage" aspect of the map is a measure of how frequently two markers are inherited together. The closer the markers are to each other physically, the less likely a recombination event will fall between and separate them. Recombination frequency thus provides an estimate of the distance between two markers. The value of the genetic map is that an inherited trait can be located on the map by following the inheritance of a DNA marker present in affected individuals, but absent in unaffected individuals, even though the molecular basis for the trait may not yet be understood. Genetic maps have been used to find the exact chromosomal location of several important disease genes, including cystic fibrosis, muscular dystrophy, sickle cell disease, Tay-Sachs disease, fragile X syndrome and many others.

An emerging class of marker for genetic analysis of the single nucleotide polymorphism, and other simple polymorphisms, e.g. deletions, double nucleotide polymorphisms, etc. SNPs are generally biallelic systems, that is, there are two alleles that a population may have for any particular marker. This means that the information content per SNP marker is relatively low when compared to microsatellite markers, which may have upwards of 10 alleles. SNPs also tend to be very population-specific; a marker that is polymorphic in one population may not be very polymorphic in another.

SNP markers offer a number of benefits that will make them an increasingly valuable tool. SNPs, found approximately every kilobase (see Wang et al. (1998) *Science* 280: 1077-1082), offer the potential for generating very high density genetic maps, which will be extremely useful for developing haplotyping systems for genes or regions of interest, and because of the nature of SNPs, they may in fact be the polymorphisms associated with the disease phenotypes under study. The low mutation rate of SNPs also makes them excellent markers for studying complex genetic traits.

Substrate screening assay. Substrate screening assays are used to determine the catalytic activity of a BLyS protein or peptide fragment on a substrate. Many suitable assays are known in the art, including the use of primary or cultured cells, genetically modified cells (e.g., where DNA encoding the BLyS polymorphism to be studied is introduced into the cell within an artificial construct), cell-free systems, e.g. microsomal preparations or recombinantly produced enzymes in a suitable buffer, or in animals, including human clinical trials.

Typically a detectably labeled substrate is input into the assay system, and the generation of labeled triglyceride is measured over time. The choice of detection system is determined by the substrate and the specific assay parameters. Assays are conventionally run, and will include negative and positive controls, varying concentrations of substrate and enzyme, etc. Exemplary assays may be found in the literature, as described above.

Pharmacokinetic parameters. Pharmacokinetic parameters provide fundamental data for designing safe and effective dosage regimens. A drug's volume of distribution, clearance, and the derived parameter, half-life, are particularly important, as they determine the degree of fluctuation between a maximum and minimum plasma concentration during a dosage interval, the magnitude of steady state concentration and the time to reach steady state plasma concentration upon chronic dosing. Parameters derived from in vivo drug administration are useful in determining the clinical effect of a particular BLyS genotype.

Expression assay. An assay to determine the effect of a sequence polymorphism on BLyS expression. Expression assays may be performed in cell-free extracts, or by transforming cells with a suitable vector. Alterations in expression may occur in the basal level that is expressed in one or more cell types, or in the effect that an expression modifier has on the ability of the gene to be inhibited or induced. Expression levels of a variant alleles are compared by various methods known in the art. Methods for determining promoter or enhancer strength include quantitation of the expressed natural protein; insertion of the variant control element into a vector with a reporter gene such as galactosidase, luciferase, chloramphenicol acetyltransferase, etc. that provides for convenient quantitation; and the like.

Gel shift or electrophoretic mobility shift assay provides a simple and rapid method for detecting DNA-binding proteins (Ausubel, F. M. et al. (1989) In: Current Protocols in Molecular Biology, Vol. 2, John Wiley and Sons, New York). This method has been used widely in the study of sequence-specific DNA-binding proteins, such as transcription factors. The assay is based on the observation that complexes of protein and DNA migrate through a nondenaturing polyacrylamide gel more slowly than free DNA fragments or double-stranded oligonucleotides. kilo The gel shift assay is performed by incubating a purified protein, or a complex mixture of proteins (such as nuclear or cell extract preparations), with an end-labeled DNA fragment containing the putative protein binding site. The reaction products are then analyzed on a nondenaturing polyacrylamide gel. The specificity of the DNA-binding protein for the putative binding site is established by competition experiments using DNA fragments or oligonucleotides containing a binding site for the protein of interest, or other unrelated DNA sequences.

Expression assays can be used to detect differences in expression of polymorphisms with respect to tissue specificity, expression level, or expression in response to exposure to various substrates, and/or timing of expression during development.

Genotyping BLyS genotyping is performed by DNA or RNA sequence and/or hybridization analysis of any convenient sample from a patient, e.g. biopsy material, blood sample (serum, plasma, etc.), buccal cell sample, etc. A nucleic acid sample from an individual is analyzed for the presence of polymorphisms in BLyS, particularly those that affect the activity or expression of BLyS. Specific sequences of interest include any polymorphism that leads to changes in basal expression in one or more tissues, to changes in the modulation of BLyS expression by modifiers, or alterations in BLyS substrate specificity and/or activity.

The effect of a polymorphism in the BLyS gene sequence on the response to a particular substrate or modifier of BLyS is determined by in vitro or in vivo assays. Such assays may include monitoring the metabolism of a substrate during clinical trials to determine the BLyS biological activity, specificity or expression level. Generally, in vitro assays are useful in determining the direct effect of a particular polymorphism, while clinical studies will also detect an biological phenotype that is genetically linked to a polymorphism.

The response of an individual to the substrate or modifier can then be predicted by determining the BLyS genotype, with respect to the polymorphism. Where there is a differential distribution of a polymorphism by racial background, guidelines for drug administration can be generally tailored to a particular ethnic group.

The basal expression level in different tissue may be determined by analysis of tissue samples from individuals typed for the presence or absence of a specific polymorphism. Any convenient method may be use, e.g. ELISA, RIA, etc. for protein quantitation, northern blot or other hybridization analysis, quantitative RT-PCR, etc. for mRNA quantitation. The tissue specific expression is correlated with the genotype.

The alteration of BLyS expression in response to a modifier is determined by administering or combining the candidate modifier with an expression system, e.g. animal, cell, in vitro transcription assay, etc. The effect of the modifier on BLyS transcription and/or steady state mRNA levels is determined. As with the basal expression levels, tissue specific interactions are of interest. Correlations are made between the ability of an expression modifier to affect BLyS activity, and the presence of the provided polymorphisms. A panel of different modifiers, cell types, etc. may be screened in order to determine the effect under a number of different conditions.

A BLyS polymorphism that results in altered biological activity or specificity is determined by a variety of assays known in the art. The ligand may be tested for formation of triglyceride product in vitro, for example in defined buffer, or in cell or subcellular lysates, where the ability of a substrate to be acted on by BLyS under physiologic conditions is determined. Where there are not significant issues of toxicity from the substrate or products(s), in vivo human trials maybe utilized, as previously described.

The genotype of an individual is determined with respect to the provided BLyS gene polymorphisms. The genotype is useful for determining the presence of a phenotypically evident polymorphism, and for determining the linkage of a polymorphism to phenotypic change.

Any of a number of techniques known to those skilled in the art can be used to detect a polymorphism in a BLyS gene, using an isolated polynucleotide of the invention. These include, but are not limited to, direct sequencing of the interval from affected individuals (Chadwick et al. (1996) *Biotechniques* 20:676-683); and hybridization with one or more probes derived from a region of a BLyS gene, including allele-specific oligonucleotide hybridization (Wong and Senadheera (1997) *Clin. Chem.* 43:1857-1861). The region being detected can optionally be amplified by known techniques, including, but not limited to, a polymerase chain reaction. Other analytical techniques include, but are not limited to, single-strand conformation analysis; restriction length polymorphism (RFLP) analysis; enzymatic mismatch cleavage techniques such as glycosylase mediated polymorphism detection (Vaughan and McCarthy (1998) *Nucl. Acids Res.* 26:810-815); heteroduplex PCR (Deuter and Muller (1998) *Hum. Mutat.* 11:84-89); and fiberoptic DNA sensor array techniques (Healey et al. (1997) *Anal. Biochem.* 251: 270-279). Automated methods of detecting polymorphisms have been developed and can be used in the methods of the present invention. See, for example, Marshall and Hodgson (1998) *Nature Biotechnol* 16:27-31. Other methods include, for example, PCR-RFLP. Hani et al. (1998) *J. Clin. Invest.* 101:521-526.

Treatment Methods

The present invention hither provides a method of treating an individual clinically diagnosed with a condition associated with BLyS activity. The methods generally comprises analyzing a polynucleotide sample from an individual clinically diagnosed with a condition associated with BLyS activity for the presence or absence of a BLyS gene polymorphism. The presence of a BLyS gene polymorphism associated with a condition relating to abnormal hematological cell growth confirms the clinical diagnosis of a condition associated with BLyS activity. A treatment plan that is most effective for individuals clinically diagnosed as having a condition associated with BLyS activity is then selected on the basis of the detected BLyS polymorphism. Genotype information obtained as described above can be used to predict the response of the individual to a particular BLyS substrate (e.g., activator or inhibitor of BLyS biological activity), or modifier of BLyS gene expression. Thus, the invention further provides a method for predicting a patient's likelihood to respond to a drug treatment for a condition associated with BLyS activity, comprising determining a patient's genotype in a BLyS gene, wherein the presence of a BLyS allele associated with a condition associated with BLyS activity is predictive of the patient's likelihood to respond to a drug treatment for the condition. Where an expression modifier inhibits BLyS expression, then drugs that are a BLyS substrate will be metabolized more slowly if the modifier is co-administered. Where an expression modifier induces BLyS expression, a co-administered substrate will typically be metabolized more rapidly. Similarly, changes in BLyS activity will affect the metabolism of an administered drug. The pharmacokinetic effect of the interaction will depend on the metabolite that is produced, e.g. a prodrug is metabolized to an active form, a drug is metabolized to an inactive form, an environmental compound is metabolized to a toxin, etc. Consideration is given to the route of administration, drug-drug interactions, drug dosage, etc.

Thus, another aspect of the invention provides methods for tailoring an individual's prophylactic, or therapeutic treatment with BLyS expression and/or activity modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Agents that have a stimulatory or inhibitory effect on BLyS expression levels or BLyS biological activity can be administered to individuals to treat (prophylactically or therapeutically) disorders associated with BLyS activity. Additionally, the isolated polymorphic BLyS nucleic acid molecules of the present invention, as well as agents, or modulators which have a stimulatory or inhibitory effect on BLyS expression levels or BLyS biological activity can be administered to individuals to treat a condition associated with BLyS activity. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a modulator of BLyS expression or biological activity ("a BLyS modulator") as well as tailoring the dosage and/or therapeutic regimen of treatment with a BLyS modulator.

Determination of how a given BLyS polymorphism is predictive of a patient's likelihood of responding to a given drug treatment for a condition relating to abnormal fat storage can be accomplished by determining the genotype of the patient in the BLyS gene, as described above, and/or determining the effect of the drug on BLyS gene expression, and/or determining the effect of the drug on BLyS biological activity. Information generated from one or more of these approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a BLyS molecule or BLyS modulator, such as a modulator identified by one of the exemplary screening assays described herein.

Microarrays

The invention further provides an array of oligonucleotides (also referred to herein as "probes"), where discrete positions on the array are complementary to one or more of the provided polymorphic sequences, e.g. oligonucleotides of at least 12 nt, at least about 15 nt, at least about 18 nt, at least about 20 nt, or at least about 25 nt, or longer, and including the sequence flanking the polymorphic position. Such an array may comprise a series of oligonucleotides, each of which can specifically hybridize to a different polymorphism. For examples of arrays, see Hacia et al. (1996) Nat. Genet. 14:441-447 and DeRisi et al. (1996) Nat. Genet. 14:457-460.

An array may include all or a subset of the polymorphisms listed above. One or more polymorphic forms may be present in the array. In some embodiments, an array includes at least 2 different polymorphic sequences, i.e. polymorphisms located at unique positions within the locus, and may include as many all of the provided polymorphisms. Arrays of interest may further comprise sequences, including polymorphisms, of other genetic sequences, particularly other sequences of interest for pharmacogenetic screening, including, but not limited to, other genes associated with hematological malignancies, including but not limited to those associated with B-CLL such as zap-70, CD38 etc., or an equivalent thereof in another species. The oligonucleotide sequence on the array is generally at least about 12 nt in length, at least about 15 nt, at least about 18 nt, at least about 20 nt, or at least about 25 nt, or may be the length of the provided polymorphic sequences, or may extend into the flanking regions to generate fragments of 100 to 200 nt in length. For examples of arrays, see Ramsay (1998) Nature Biotech. 16:40-44; Hacia et al (1996) Nature Genetics 14:441-447; Lockhart et al (1996) Nature Biotechnol. 14:1675-1680; and De Risi et al. (1996) Nature Genetics 14:457-460.

A number of methods are available for creating microarrays of biological samples, such as arrays of DNA samples to be used in DNA hybridization assays. Exemplary are PCT Application Serial. No. WO95/35505, published Dec. 28, 1995; U.S. Pat. No. 5,445,934, issued Aug. 29, 1995; and Drnanac et al. (1993) Science 260:1649-1652. Yershov et al, (1996) Genetics 93:4913-4918 describe an alternative construction of an oligonucleotide array. The construction and use of oligonucleotide arrays is reviewed by Ramsay (1998) supra.

Methods of using high density oligonucleotide arrays are known in the art. For example, Milosavljevic et al. (1996) Genomics 37:77-86 describe DNA sequence recognition by hybridization to short oligomers. See also, Drmanac et al. (1998) Nature Biotech. 16:54-58; and Drnanac and Drmanac (1999) Methods Enzymol 303:165-178; The use of arrays for identification of unknown mutations is proposed by Ginot (1997) Human Mutation 10:1-10.

Detection of known mutations is described in Hacia et al. (1996) Nat. Genet. 14:441-447; Cronin et al. (1996) Human Mut. 7:244-255; and others. The use of arrays in genetic mapping is discussed in Chee et al. (1996) Science 274:610-613; Sapolsky and Lishutz (1996) Genomics 33:445-456; etc. Shoemaker et al. (1996) Nat. Genet. 14:450-456 perform quantitative phenotypic analysis of yeast deletion mutants using a parallel bar-coding strategy.

Quantitative monitoring of gene expression patterns with a complementary DNA microarray is described in Schena et al. (1995) Science 270:467. DeRisi et al (1997) Science 270:680-686 explore gene expression on a genomic scale. Wodicka et al. (1997) Nat. Biotech. 15:1-15 perform genome wide expression monitoring in S. cerevisiae.

A DNA sample is prepared in accordance with conventional methods, e.g. lysing cells, removing cellular debris, separating the DNA from proteins, lipids or other components present in the mixture and then using the isolated DNA for cleavage. See Molecular Cloning, A Laboratory Manual, 2nd ed. (eds. Sambrook et al.) CSH Laboratory Press, Cold Spring Harbor, N.Y. 1989. Generally, at least about 0.5 μg of DNA will be employed, usually at least about 5 μg of DNA, while less than 50 μg of DNA will usually be sufficient.

The nucleic acid samples are cleaved to generate probes. It will be understood by one of skill in the art that any method of random cleavage will generate a distribution of fragments, varying in the average size and standard deviation. Usually the average size will be at least about 12 nucleotides in length, more usually at least about 20 nucleotides in length, and preferably at least about 35 nucleotides in length. Where the variation in, size is great, conventional methods may be used to remove the large and/or small regions of the fragment population.

It is desirable, but not essential to introduce breaks randomly, with a method which does not act preferentially on specific sequences. Preferred methods produce a reproducible pattern of breaks. Methods for introducing random breaks or nicks in nucleic acids include reaction with Fenton reagent to produce hydroxyl radicals and other chemical cleavage systems, integration mediated by retroviral integrase, partial digestion with an ultra-frequent cutting restriction enzymes, partial digestion of single stranded with S1 nuclease, partial digestion with DNAse I in the absence or presence of $Mn^{++}$, etc.

The fragmented nucleic acid samples are denatured and labeled. Labeling can be performed according to methods well known in the art, using any method that provides for a detectable signal either directly or indirectly from the nucleic acid fragment. In a preferred embodiment, the fragments are end-labeled, in order to minimize the steric effects of the label. For example, terminal transferase may be used to conjugate a labeled nucleotide to the nucleic acid fragments. Suitable labels include biotin and other binding moieties; fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), and the like. Where the label is a binding moiety, the detectable label is conjugated to a second stage reagent, e.g. avidin, streptavidin, etc. that specifically binds to the binding moiety, for example a fluorescent probe attached to streptavidin. Incorporation of a fluorescent label using enzymes such as reverse transcriptase or DNA polymerase, prior to fragmentation of the sample, is also possible.

Each of the labeled genome samples is separately hybridized to an array of oligonucleotide probes. Hybridization of the labeled sequences is accomplished according to methods well known in the art. Hybridization can be carried out under conditions varying in stringency, preferably under conditions of high stringency, e.g. 6×SSPE, at 65° C., to allow for hybridization of complementary sequences having extensive homology, usually having no more than one or two mismatches in a probe of 25 nucleotides in length, i.e. at least 95% to 100% sequence identity.

High density microarrays of oligonucleotides are known in the art and are commercially available. The sequence of oligonucleotides on the array will correspond to the known target sequences of one of the genomes, as previously described. Arrays of interest for the subject methods will generally comprise at least about $10^3$ different sequences, usually at least about $10^4$ different sequences, and may comprise $10^5$ or more different sequences. The length of oligonucleotide present on the array is an important factor in how sensitive hybridization will be to the presence of a mismatch. Usually oligonucleotides will be at least about 12 nt in length, more usually at least about 15 nt in length, preferably at least about 20 nt in length and more preferably at least about 25 nt in length, and will be not longer than about 35 nt in length, usually not more than about 30 nt in length.

Methods of producing large arrays of oligonucleotides are described in U.S. Pat. No. 5,134,854 (Pirrung et al.), and U.S. Pat. No. 5,445,934 (Fodor et al.) using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in International Patent application WO 95/35505.

Microarrays can be scanned to detect hybridization of the labeled genome samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. (1996) *Genome Res.* 6:639. A scan, using the appropriate excitation line, is performed for each fluorophore used. The digital images generated from the scan are then combined for subsequent analysis. For any particular array element, the ratio of the fluorescent signal from one Nucleic acid sample is compared to the fluorescent signal from the other Nucleic acid sample, and the relative signal intensity determined.

Methods for analyzing the data collected by fluorescence detection are known in the art. Data analysis includes the steps of determining fluorescent intensity as a function of substrate position from the data collected, removing outliers, i.e. data deviating from a predetermined statistical distribution, and calculating the relative binding affinity of the targets from the remaining data. The resulting data may be displayed as an image with the intensity in each region varying according to the binding affinity between targets and probes.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Search for SNPs Associated with Increased Risk of Developing NHL

We genotyped 9 tagSNPs within the BLyS gene in a clinic-based study of 441 incident Caucasian NHL cases and 475 frequency matched Caucasian controls seen at the Mayo Clinic from 2002-2005. We evaluated the association of individual SNPs as well as haplotypes from the BLyS gene with risk of NHL. We also jointly tested the main effects for all independent ($r^2<0.25$) SNPs using a multivariate logistic regression (MLR) model. As a secondary analysis, for those SNPs showing significant results (<5% significance), we evaluated associations between those who had all high risk alleles at the SNPs of interest compared to those who had all low risk alleles at the SNPs of interest. Additionally, we evaluated serum BLyS levels by ELISA in these same subjects. Serum BLyS levels were determined by ELISA.

Results: In the individual single SNP logistic regression analysis, 3 of the 9 tagSNPs were significant at p<0.05. Those three SNPs have been identified as the major alleles of following: rs12583006 (SEQ ID NO:5), rs1224141 (SEQ ID NO:6), and rs12428930 (rs283296) (SEQ ID NO:7). Haplotype and MLR results were nonsignificant. However, when we categorized participants into low and high risk groups based on risk alleles at the three statistically significant SNPs, we found the high risk variant (i.e., the presence of all three major alleles) had an odds ratio (OR) of 2.086 (p=0.0001) for risk of B-cell NHL. When the analysis was restricted by histologic subtype we found that diffuse large B-cell lymphoma or follilcular lymphoma grade 3 had an OR of 3.163 (p=0.01), follicular lymphoma grade I/II had an OR=2.547 (p=0.046), and chronic lymphocytic leukemia (CLL) had an OR=1.238 (p=0.13). Because there was not a significant correlation of the high risk variant with CLL, we performed an additional analysis in which we included all B cell NHL cases excluding CLL and the OR was 2.799 (p=0.0001).

Example 2

Measurement of BLyS Levels Inpatients with Patients with High and Low Risk Variant Alleles We next wanted to determine if serum BLyS levels correlated with either the high or low risk variant. The mean serum BLyS level in those individuals (untreated cases and controls) who carried the low risk variant at all three SNPs was significantly lower (p=0.0061) at 1.3 ng/ml (n=25, range: undetectable-4.4 ng/ml) compared to 4.3 ng/ml in those with the high risk variant (n=74, range: undetectable-66.8 ng/ml).

BLyS levels were determined using a BLyS ELISA as follows. ELISA plates were coated with 1 μg/ml anti-BLyS (ZymoGenetics, Seattle, Wash.) and BLyS was detected with 1 μg/ml biotinylated anti-BLyS (ZymoGenetics, Seattle, Wash.) followed by streptavidin-HRP and TMB substrate as described in Novak et al. *Blood* 2004, supra. Patient serum samples were diluted 1:5 and 1:25 in triplicate and BLyS serum levels were calculated from a standard curve generated with recombinant human BLyS (ZymoGenetics, Seattle, Wash.) in 20% human sera. The detection limit of purified BLyS was 300 pg/ml.

Conclusions: In summary, we have found that genetic variation in the BLyS gene is significantly associated with an increased risk of developing B-cell NHL, particularly follicular and large B-cell lymphoma. Additionally, this increased lymphoma risk is associated with an increase in serum BLyS levels.

While the present invention has been described with reference to the specific embodiments thereof, it is to be understood by those skilled in the art that various changes may be made and an equivalence may be substituted without departing from the true spirit and scope of the invention. In addition, many modifications may be made to adapt a particular situation, material, composition of matter, process, process step or steps, to the object, spirit and scope of the present invention. All such modifications are intended to be within the scope of the claims appended hereto.

We claim:

1. A method of detecting a propensity of a human to develop a condition selected from the group consisting of B-cell non-Hodgkin's lymphoma, diffuse large B-cell lymphoma, follicular lymphoma grade 1, follicular lymphoma grade 2, and follicular lymphoma grade 3, wherein said method comprises:
   (a) detecting in a polynucleotide sample derived from said human the presence of a polymorphism in a B-lymphocyte stimulator (BLyS) gene, wherein said polymorphism is selected from the group consisting of a T allele at rs12583006, a T allele at rs122414, and an A allele at rs1248930, and
   (b) classifying said human as having an increased propensity to develop said condition if said polymorphism is present.

2. The method of claim 1, wherein said method comprises detecting in said polynucleotide sample the presence of two or more polymorphisms selected from said group, and classifying said human as having an increased propensity to develop said condition if said two or more polymorphisms are present.

3. The method of claim 2, wherein said method comprises detecting in said polynucleotide sample the presence of three polymorphisms selected from said group and classifying said human as having an increased propensity to develop said condition if said three polymorphisms are present.

4. The method of claim 1, wherein the presence of said polymorphism is determined by contacting a polynucleotide from said human with a polynucleotide probe which is capable of hybridizing to said polymorphism under stringent conditions; and determining whether hybridization has occurred, thereby indicating the presence of said polymorphism.

5. A method for identifying a human having an increased risk of developing a condition selected from the group consisting of B-cell non-Hodgkin's lymphoma, diffuse large B-cell lymphoma, follicular lymphoma grade 1, follicular lymphoma grade 2, and follicular lymphoma grade 3, wherein said method comprises:
   (a) detecting the presence of a polymorphism selected from the group consisting of a T allele at rs12583006, a T allele at rs122414, and an A allele at rs1248930 in a polynucleotide sample from said human, and
   (b) classifying said human as having increased risk of developing said condition based on the presence of said polymorphism.

6. The method of claim 4, wherein said method comprises detecting the presence of two or more polymorphisms selected from said group in said polynucleotide sample, and classifying said human as having increased risk of developing said condition when said two or more polymorphisms are present.

7. The method of claim 6, wherein said method comprises detecting the presence of three polymorphisms selected from said group in said polynucleotide sample, and classifying said human as having increased risk of developing said condition when said three polymorphisms are present.

8. The method of claim 4, wherein the presence of said polymorphism is detected by contacting said polynucleotide sample with a polynucleotide probe which is capable of hybridizing to said polymorphism under stringent conditions; and determining that hybridization has occurred, thereby indicating the presence of said polymorphism.

* * * * *

UNITED STATES PATENT AND TRADEMARK OFFICE
CERTIFICATE OF CORRECTION

| | | |
|---|---|---|
| PATENT NO. | : 8,003,325 B2 | Page 1 of 1 |
| APPLICATION NO. | : 12/323861 | |
| DATED | : August 23, 2011 | |
| INVENTOR(S) | : Stephen M. Ansell | |

It is certified that error appears in the above-identified patent and that said Letters Patent is hereby corrected as shown below:

Column 50, line 33 (Claim 6), please delete "4" and insert --5-- therefor;

Column 50, line 44 (Claim 8), please delete "4" and insert --5-- therefor.

Signed and Sealed this
Twenty-second Day of May, 2012

David J. Kappos
*Director of the United States Patent and Trademark Office*

SEQUENCE LISTING

<160> NUMBER OF SEQ ID NOS: 7

<210> SEQ ID NO 1
<211> LENGTH: 1149
<212> TYPE: DNA
<213> ORGANISM: homo sapiens
<220> FEATURE:
<221> NAME/KEY: CDS
<222> LOCATION: (173)...(1027)

<400> SEQUENCE: 1
gaattcggca cgaggcagaa aggagaaaat tcaggataac tctcctgagg ggtgagccaa      60
gccctgccat gtagtgcacg caggacatca acaaacacag ataacaggaa atgatccatt     120
ccctgtggtc acttattcta aaggccccaa ccttcaaagt tcaagtagtg at atg gat    178
                                                         Met Asp
                                                           1 gac tcc aca gaa agg gag cag tca cgc ctt act tct tgc ctt aag aaa      226
Asp Ser Thr Glu Arg Glu Gln Ser Arg Leu Thr Ser Cys Leu Lys Lys
        5                  10                  15 aga gaa gaa atg aaa ctg aag gag tgt gtt tcc atc ctc cca cgg aag      274
Arg Glu Glu Met Lys Leu Lys Glu Cys Val Ser Ile Leu Pro Arg Lys
 20                  25                  30 gaa agc ccc tct gtc cga tcc tcc aaa gac gga aag ctg ctg gct gca      322
Glu Ser Pro Ser Val Arg Ser Ser Lys Asp Gly Lys Leu Leu Ala Ala
 35                  40                  45                  50 acc ttg ctg ctg gca ctg ctg tct tgc tgc ctc acg gtg gtg tct ttc      370
Thr Leu Leu Leu Ala Leu Leu Ser Cys Cys Leu Thr Val Val Ser Phe
                 55                  60                  65 tac cag gtg gcc gcc ctg caa ggg gac ctg gcc agc ctc cgg gca gag      418
Tyr Gln Val Ala Ala Leu Gln Gly Asp Leu Ala Ser Leu Arg Ala Glu
             70                  75                  80 ctg cag ggc cac cac gcg gag aag ctg cca gca gga gca gga gcc ccc      466
Leu Gln Gly His His Ala Glu Lys Leu Pro Ala Gly Ala Gly Ala Pro
         85                  90                  95 aag gcc ggc ctg gag gaa gct cca gct gtc acc gcg gga ctg aaa atc      514
Lys Ala Gly Leu Glu Glu Ala Pro Ala Val Thr Ala Gly Leu Lys Ile
    100                 105                 110

```
ttt gaa cca cca gct cca gga gaa ggc aac tcc agt cag aac agc aga      562
Phe Glu Pro Pro Ala Pro Gly Glu Gly Asn Ser Ser Gln Asn Ser Arg
115                 120                 125                 130 aat aag cgt gcc gtt cag ggt cca gaa gaa aca gtc act caa gac tgc      610
Asn Lys Arg Ala Val Gln Gly Pro Glu Glu Thr Val Thr Gln Asp Cys
                135                 140                 145 ttg caa ctg att gca gac agt gaa aca cca act ata caa aaa gga tct      658
Leu Gln Leu Ile Ala Asp Ser Glu Thr Pro Thr Ile Gln Lys Gly Ser
            150                 155                 160 tac aca ttt gtt cca tgg ctt ctc agc ttt aaa agg gga agt gcc cta      706
Tyr Thr Phe Val Pro Trp Leu Leu Ser Phe Lys Arg Gly Ser Ala Leu
        165                 170                 175 gaa gaa aaa gag aat aaa ata ttg gtc aaa gaa act ggt tac ttt ttt      754
Glu Glu Lys Glu Asn Lys Ile Leu Val Lys Glu Thr Gly Tyr Phe Phe
    180                 185                 190 ata tat ggt cag gtt tta tat act gat aag acc tac gcc atg gga cat      802
Ile Tyr Gly Gln Val Leu Tyr Thr Asp Lys Thr Tyr Ala Met Gly His
195                 200                 205                 210 cta att cag agg aag aag gtc cat gtc ttt ggg gat gaa ttg agt ctg      850
Leu Ile Gln Arg Lys Lys Val His Val Phe Gly Asp Glu Leu Ser Leu
                215                 220                 225 gtg act ttg ttt cga tgt att caa aat atg cct gaa aca cta ccc aat      898
Val Thr Leu Phe Arg Cys Ile Gln Asn Met Pro Glu Thr Leu Pro Asn
            230                 235                 240 aat tcc tgc tat tca gct ggc att gca aaa ctg gaa gaa gga gat gaa      946
Asn Ser Cys Tyr Ser Ala Gly Ile Ala Lys Leu Glu Glu Gly Asp Glu
        245                 250                 255 ctc caa ctt gca ata cca aga gaa aat gca caa ata tca ctg gat gga      994
Leu Gln Leu Ala Ile Pro Arg Glu Asn Ala Gln Ile Ser Leu Asp Gly
    260                 265                 270 gat gtc aca ttt ttt ggt gca ttg aaa ctg ctg tgacctactt acaccatgtc   1047
Asp Val Thr Phe Phe Gly Ala Leu Lys Leu Leu
275                 280                 285 tgtagctatt ttcctcccctt tctctgtacc tctaagaaga aagaatctaa ctgaaaatac   1107
caaaaaaaaa aaaaaaaaaa aaaaaaccct cgagcggccg cc                       1149

<210> SEQ ID NO 2
<211> LENGTH: 285
<212> TYPE: PRT
<213> ORGANISM: homo sapien

<400> SEQUENCE: 2

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125
```

```
Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 3
<211> LENGTH: 1680
<212> TYPE: DNA
<213> ORGANISM: Mus musculus
<220> FEATURE:
<221> NAME/KEY: CDS
<222> LOCATION: (164)...(1093)

<400> SEQUENCE: 3
tactcactat agggctcgag cggccgcccg ggcaggtgct cctgggggaa cccagccctg      60
ccatgctctg agggcagtct cccaggacac agatgacagg aaatgaccca cccctgtggt     120
cacttactcc aaaggcctag accttcaaag tgctcctcgt gga atg gat gag tct     175
                                                Met Asp Glu Ser
                                                  1 gca aag acc ctg cca cca ccg tgc ctc tgt ttt tgc tcc gag aaa gga    223
Ala Lys Thr Leu Pro Pro Pro Cys Leu Cys Phe Cys Ser Glu Lys Gly
  5              10                  15                  20 gaa gat atg aaa gtg gga tat gat ccc atc act ccg cag aag gag gag    271
Glu Asp Met Lys Val Gly Tyr Asp Pro Ile Thr Pro Gln Lys Glu Glu
                 25                  30                  35 ggt gcc tgg ttt ggg atc tgc agg gat gga agg ctg ctg gct gct acc    319
Gly Ala Trp Phe Gly Ile Cys Arg Asp Gly Arg Leu Leu Ala Ala Thr
             40                  45                  50 ctc ctg ctg gcc ctg ttg tcc agc agt ttc aca gcg atg tcc ttg tac    367
Leu Leu Leu Ala Leu Leu Ser Ser Ser Phe Thr Ala Met Ser Leu Tyr
         55                  60                  65 cag ttg gct gcc ttg caa gca gac ctg atg aac ctg cgc atg gag ctg    415
Gln Leu Ala Ala Leu Gln Ala Asp Leu Met Asn Leu Arg Met Glu Leu
     70                  75                  80 cag agc tac cga ggt tca gca aca cca gcc gcc gcg ggt gct cca gag    463
Gln Ser Tyr Arg Gly Ser Ala Thr Pro Ala Ala Ala Gly Ala Pro Glu
 85                  90                  95                 100 ttg acc gct gga gtc aaa ctc ctg aca ccg gca gct cct cga ccc cac    511
Leu Thr Ala Gly Val Lys Leu Leu Thr Pro Ala Ala Pro Arg Pro His
                105                 110                 115
```

```
aac tcc agc cgc ggc cac agg aac aga cgc gct ttc cag gga cca gag       559
Asn Ser Ser Arg Gly His Arg Asn Arg Arg Ala Phe Gln Gly Pro Glu
            120                 125                 130 gaa aca gaa caa gat gta gac ctc tca gct cct cct gca cca tgc ctg       607
Glu Thr Glu Gln Asp Val Asp Leu Ser Ala Pro Pro Ala Pro Cys Leu
        135                 140                 145 cct gga tgc cgc cat tct caa cat gat gat aat gga atg aac ctc aga       655
Pro Gly Cys Arg His Ser Gln His Asp Asp Asn Gly Met Asn Leu Arg
150                 155                 160 aac atc att caa gac tgt ctg cag ctg att gca gac agc gac acg ccg       703
Asn Ile Ile Gln Asp Cys Leu Gln Leu Ile Ala Asp Ser Asp Thr Pro
165                 170                 175                 180 act ata cga aaa gga act tac aca ttt gtt cca tgg ctt ctc agc ttt       751
Thr Ile Arg Lys Gly Thr Tyr Thr Phe Val Pro Trp Leu Leu Ser Phe
                185                 190                 195 aaa aga gga aat gcc ttg gag gag aaa gag aac aaa ata gtg gtg agg       799
Lys Arg Gly Asn Ala Leu Glu Glu Lys Glu Asn Lys Ile Val Val Arg
            200                 205                 210 caa aca ggc tat ttc ttc atc tac agc cag gtt cta tac acg gac ccc       847
Gln Thr Gly Tyr Phe Phe Ile Tyr Ser Gln Val Leu Tyr Thr Asp Pro
        215                 220                 225 atc ttt gct atg ggt cat gtc atc cag agg aag aaa gta cac gtc ttt       895
Ile Phe Ala Met Gly His Val Ile Gln Arg Lys Lys Val His Val Phe
230                 235                 240 ggg gac gag ctg agc ctg gtg acc ctg ttc cga tgt att cag aat atg       943
Gly Asp Glu Leu Ser Leu Val Thr Leu Phe Arg Cys Ile Gln Asn Met
245                 250                 255                 260 ccc aaa aca ctg ccc aac aat tcc tgc tac tcg gct ggc atc gcg agg       991
Pro Lys Thr Leu Pro Asn Asn Ser Cys Tyr Ser Ala Gly Ile Ala Arg
                265                 270                 275 ctg gaa gaa gga gat gag att cag ctt gca att cct cgg gag aat gca      1039
Leu Glu Glu Gly Asp Glu Ile Gln Leu Ala Ile Pro Arg Glu Asn Ala
            280                 285                 290 cag att tca cgc aac gga gac gac acc ttc ttt ggt gcc cta aaa ctg      1087
Gln Ile Ser Arg Asn Gly Asp Asp Thr Phe Phe Gly Ala Leu Lys Leu
        295                 300                 305 ctg taa ctcacttgct ggagtgcgtg atcccttcc ctcgtcttct ctgtacctcc        1143
Leu * gagggagaaa cagacgactg gaaaaactaa aagatgggga aagccgtcag cgaaagtttt    1203
ctcgtgaccc gttgaatctg atccaaacca ggaaatataa cagacagcca caaccgaagt    1263
gtgccatgtg agttatgaga aacggagccc gcgctcagaa agaccggatg aggaagaccg    1323
ttttctccag tcctttgcca acacgcaccg caaccttgct ttttgccttg ggtgacacat    1383
gttcagaatg cagggagatt tccttgtttt gcgatttgcc atgagaagag ggcccacaac    1443
tgcaggtcac tgaagcattc acgctaagtc tcaggattta ctctcccttc tcatgctaag    1503
tacacacacg ctcttttcca ggtaatacta tgggatacta tggaaaggtt gtttgttttt    1563
aaatctagaa gtcttgaact ggcaatagac aaaaatcctt ataaattcaa gtgtaaaata    1623
aacttaatta aaaaggtaaa aaaaaaaaaa aaaaaaaaaa aaaaaaaaaa aaaaaaa      1680

<210> SEQ ID NO 4
<211> LENGTH: 309
<212> TYPE: PRT
<213> ORGANISM: Mus musculus

<400> SEQUENCE: 4

Met Asp Glu Ser Ala Lys Thr Leu Pro Pro Pro Cys Leu Cys Phe Cys
1               5                   10                  15
```

Ser Glu Lys Gly Glu Asp Met Lys Val Gly Tyr Asp Pro Ile Thr Pro
       20                   25                  30

Gln Lys Glu Glu Gly Ala Trp Phe Gly Ile Cys Arg Asp Gly Arg Leu
       35                   40                  45

Leu Ala Ala Thr Leu Leu Ala Leu Leu Ser Ser Phe Thr Ala
50                      55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
               100                 105                 110

Pro Arg Pro His Asn Ser Ser Arg Gly His Arg Asn Arg Arg Ala Phe
               115                 120                 125

Gln Gly Pro Glu Glu Thr Glu Gln Asp Val Asp Leu Ser Ala Pro Pro
130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
                180                 185                 190

Leu Leu Ser Phe Lys Arg Gly Asn Ala Leu Glu Glu Lys Glu Asn Lys
                195                 200                 205

Ile Val Val Arg Gln Thr Gly Tyr Phe Phe Ile Tyr Ser Gln Val Leu
210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
                260                 265                 270

Gly Ile Ala Arg Leu Glu Glu Gly Asp Glu Ile Gln Leu Ala Ile Pro
                275                 280                 285

Arg Glu Asn Ala Gln Ile Ser Arg Asn Gly Asp Asp Thr Phe Phe Gly
                290                 295                 300

Ala Leu Lys Leu Leu
305

<210> SEQ ID NO 5
<211> LENGTH: 601
<212> TYPE: DNA
<213> ORGANISM: homo sapien
<220> FEATURE:
<221> NAME/KEY: allele
<222> LOCATION: 301
<223> OTHER INFORMATION: w=T

<400> SEQUENCE: 5
tacttaagaa ggatttgttg gaaaaataaa aactctttta aaataggttg aatgtggcta      60
ctactgtact actatagaga ctgtacgctt ggggctttag ctgccccgga ggctttgtta     120
ttcctttctt tcatgctgtc ctcattcact accattcttc ctgttaggat gcttttccat     180
acttccagca gaacagagtc tgccatagtg actaacgaat catgttttc ctggggcaca      240 ggcatggata cctttcttgt ataagattaa taaagaatc ctcagagtgg accaaaatgc      300

| | |
|---|---|
| wctgctccta tcaaaatatc tgaaaattga cataaaaatg tgttagaaaa gctttatagt | 360 |
| tataaaggaa ttatagtttt taacaatata ttttcatctt taaataccaa ggagaatttc | 420 |
| ttaacagatt ttcttatgtg accacaccct ttaatagtat gtatttatac aaactcaaac | 480 |
| ttatttagct actgctatgt tatttcaagt tttaaataca ttcatgtgtt gcttaataac | 540 |
| agggatatag tctcagggat acattctgca tccctgggca atttcatcat tgtgcaaaca | 600 |
| t | 601 |

<210> SEQ ID NO 6
<211> LENGTH: 454
<212> TYPE: DNA
<213> ORGANISM: homo sapien
<220> FEATURE:
<221> NAME/KEY: allele
<222> LOCATION: 254
<223> OTHER INFORMATION: K = T

<400> SEQUENCE: 6

| | |
|---|---|
| ctaagaccag atctatgttg aatgagaaag aaagtcttaa aaggctgaat aggagataag | 60 |
| ttgaaatagc tgaaatagtt gaaattcgat aatagctatc aaatttccta aagcgaattg | 120 |
| ccttggaaaa gtcgagtaac tttgtctgga acaaggacaa ttattcattc tgcatcccta | 180 |
| ggcaatttca ccattgtgca acatcagag catacttaca caacttcagt ggctgtaatt | 240 |
| taaacctcat tatkgaaaca tcaattttat atcttatttt ctcttctgaa gaacagttct | 300 |
| tgaaagaaac ttttctcttt aaagcacatt ttctgctaaa tgttagattt ctgctactac | 360 |
| atgagagaat agaccactgt ttttcaatgt gtaggttgtg actaagtttt aattgggctg | 420 |
| tggagactaa aaaggagaca tattcatggt gtca | 454 |

<210> SEQ ID NO 7
<211> LENGTH: 6199
<212> TYPE: DNA
<213> ORGANISM: homo sapien
<220> FEATURE:
<221> NAME/KEY: allele
<222> LOCATION: 1199
<223> OTHER INFORMATION: r=A

<400> SEQUENCE: 7

| | |
|---|---|
| atgatcagga tttctgtggg aaaaagtgag cgtcactggg gagagcggag atgatttaaa | 60 |
| acattaaaaa ttttcaaccc actttacatt atttctaata cttttcttatg agatcaagga | 120 |
| gaaaggctca ctttggtgct ggtacatttt caaaatcatt ctattttgtg tgtgatcact | 180 |
| cattacctaa tttatatata aatatatata tatatattaa atagacaaca gactcacaac | 240 |
| ttcaagcaat gctatctatt gcataagata atgatgttat tgtatttatt tttatctttta | 300 |
| gaaatactgc tttcctgttt tttgcagtga tataatgttt aagtaaaaaa aagtcagtag | 360 |
| aatttaaata ctagctaaat actacagatg atatttgaat gaaggaagtt tgggaaacac | 420 |
| aaaaccaagt gttctctaag gccttgctat tctaagagaa aaatgtacca agcaaacaga | 480 |
| aaacagaaga aagcaggagt tgctatgcta atttcagaca aaactgattt taaaccaaca | 540 |
| aagatttaaa aagacaaaga cagacattac ataatgggaa aggattcaat tcaacatgaa | 600 |
| gacctaaata tcctaaatat atatgcatcc aacacaggag catccggatt cataaagcaa | 660 |
| atttctagag atctttaaag agacttagat aactacacaa taatatgggg agacatcaac | 720 |
| cccccactga cagcatttaa caaatcatca aggaagaaaa ctaacaaaga tattcaggac | 780 |
| ctgaacttga cacctggcca aacagaccta atagacatct acaaagcttt ctaatccaaa | 840 |

```
acagcagaat atacattctc ctcattagca tgcagcacat actctaaaat caactacaca    900
gtcagacata aaacaatcct cggcaaattt tttaaaaagt gaaatcatac aactatactc    960
taagaccaca gtgcaacaga aacagaaatc aatactaaga aaattgctca aaatcataca   1020
attacatgga aattaaataa acagcacctg aatgactttt gagttaatga tgaaattaag   1080
gcagaaacaa agaaattctt tgaaactaat gaaaacaaag atacagcata cgagaatctc   1140
tgggacacag ctacagtcac gttaagagag aaatttataa tgctaaatcc ccacatcgra   1200
aagttaaaaa gatgtcaaat taacaaccca acattacaac aaaaggaact atagacagaa   1260
gagcaaacca actccaaagc taacagaaga caagaaataa cccaaatcag gctgaactga   1320
aggaaactga aggaaaccat acaaaagatc aacaaatcca ggtgttggtt tcttgaaaga   1380
attattacaa aataagatag actgctggca ggacaaataa aaagagagaa aatccatata   1440
aactcaataa aaaatgacaa aaaagacatt accgttgact ccacagaaat tcaaaaaacc   1500
atgagtgact actatgaaca cctctataca cacaagctag aaaacctgga atgcatggat   1560
aaattcctgg aaatatacaa tcatgtgaga ataaaccatg taggaattca attcctgaac   1620
acaccaataa tgagttccaa aactgaatca gtaataaaaa gcctactaac cagaaaaatc   1680
ccaggacaag gcagattcac agccaaattc tgccagatac ataaaaaaga gttggcatca   1740
ttctgatatg gtttgaatct gtgtcaccac ccaaaccttta ggttcaattg taatccccag   1800
tgttggaggt ggggcctggt gggaggtgac tggatcatgg tggcagactt ctcctgaatg   1860
gtttagcatc atccctcttg gtactgtcct tgtcatagtg agtgagttct catgagattt   1920
ggttgtttaa atgtgtgtaa cacctcccct ctctatctct tgctcctgct ctggtcctgt   1980
gacatgcctg ttccccctttt gccttccagc atgattagaa gcttcctgag gcctacccag   2040
aagcagatgc ctttatgatt cctgtgcagc ctgcagaacc ataagccaat taaacctctt   2100
ttctttatga actaccgagt ctcaggtatt tctttgcaga aatgtaaaaa cagcctaata   2160
cacattccta ctgaaagcat tccaaaaaaa ctgagcaaga gggactccta taactcattc   2220
catgagtcca gcatctccct gataccaaaa cctggcagag acataaaaaa acaggaaatt   2280
tcaggccagt atccttgata aactacagat gcaaagtcc tcaacaaaat actagaaaac   2340
tgaatagaga agcacatcaa aatgttaatc caccacaaac aagtaggctt tattcctggg   2400
atgcaagttt gattcagtat atacaaatca ataaatgtga ttcatcacat aaacaggacg   2460
aaaaccgaaa accacatgat catctcaata gattcagaaa agacttctga taaaattcaa   2520
catcaattta tgttaaaaac cctcagcaaa ctaaccattg aaggaacata ctccaaaaaa   2580
caagagcaat ctatgacaag cccacagcca acatcatact gaatggacaa agctgaaag   2640
cattacccctt taaaactgga acaaggcatt gctggcaaga aggtcaaata gtaacagctc   2700
ttgtctgcag ctcccagcga gatcaacgca ggtgctttct gcatttccaa ctgaggtgcc   2760
cggttcatct cactgggact ggttggacag tgggtgcagc ctacagaggg tgagccaaag   2820
cagggagggg cattgcctca cccaggaagc acaagggtc agagaatttt ctcccctacc   2880
caacggaaac tgtgagggac tgagcctgag gaactgtgca ctccggccca gatacggcac   2940
ttgtcccaca gtctttgcaa cccgcagact aggagatttc ctctggtgcc taccccacca   3000
ggaaccggga tttcaagcac aaaactgggc agccatttgg gcagacactg aacttgctgc   3060
aggagttttt ttttttttc catacccccag tggtgcctgg aacaccagta agacagaacc   3120
gttcactacc ctgaaagggg gtgctgaagc cagggaacca agtgatttgg cttagtgggt   3180
cccaccccca cagagcccag caaactaaga tccactggct tgaaattctt gcagccagca   3240
```

```
cagcagcagt ctgagatcga cctgggatgc tcaagtttgg ttgagggaga ggcgtccacc   3300
attgctgaag cttgagtagg cagttttaca gtcacagtgt aaacaaagcc accaggaagt   3360
tggaaccggg cggagcccac tgcagctcag caaggctact gtggccagac tgccagattt   3420
ctcctctctg ggcatggcat ctctgaaaaa acagcagcag ccccagtcag ggacttatag   3480
ataaaacccc catctccctg ggacagagca cccgagggaa ggggcggctg tgggcacagt   3540
ttccgcagac ttaaatgtcc ctgcctgatg gctctgaaaa gagcagcgga tctcccagca   3600
cagcgtttga gctctactaa gggtcagact gccttctcaa gtgggtctct taccccctgtg  3660
cctcctgact gggagacacc tcccagtagg ggccaacaga cacctaatac aggagagctc   3720
tggctggcat ctggcaggta ctcctctggg atgaagcttc cagaggcaga acaggcagca   3780
atcattgctg ttctgcagcc cccactggtg ataccctggc aaacagggtt gggaacggac   3840
ctctagcaaa ctccagcaga tctgcagcag aacagtctga caattagaag ggaaactaac   3900
aaacagaaag gaaagcaca tccactcaaa gaccccattt gaaggtcaat aacgtcaaag    3960
accaaaggca gataaatcca caaagatggg gagaaaccag tgcaaaaaga ctgaaaattc   4020
caaaaactag aacacctctt cacctccaaa ggatcacaac tgctcgccaa caagggaaca   4080
aaactggaca gagaatgagt ttgatgactg attagaggta ggcttcagaa ggtgggtaat   4140
aacaaactcc actgagctaa aggagtatgt tctagcccaa tgcctgaaag cgatgaacct   4200
tgaaatgagg ttagatgaat tgctaactag aataaccagt ttagagaaga atattaatga   4260
cctgatggag ctgaaaaaca cagcacgaga acttcgtgaa acatacacag gtatcaatag   4320
ccaaggtgat caagtggaag aaaggatatc agtgactgaa gataaactta atgaaataaa   4380
gcgagaagac aagattagag aaaaaggaat aaaaaggaat gaacaaagcc tccaagaaat   4440
acgagactat gtgaaaagac caactctaca tttgatggtg tacctgaaag tgacagggag   4500
aatggaacca agttggaaaa cactccccgg gctattatcc aggagaactt ccccaaccta   4560
gcaagacagg ccaaaattca aattcaggaa atatagagaa caccacaaag atactcctag   4620
agaagagcaa ccacaagaca cataattgtc acattcacca aggttgaaat gaaggaaaaa   4680
acgttaaggg cagccagaga gaaaggttgg gttacccaca aagggaagcc catccaacta   4740
atagcagatc tctctgcaga aaccctacaa gccagaagaa agtgggggc caatattcaa    4800
cattcttaaa gaaaagaatt ttcaactcag aatttcatat ccagccaaaa taaacatcct   4860
aagtgaagga gaaataaaat cctttataga caagcaaatg ctgagatatt ttatcaccac   4920
caggcctgct ttacaagaac tcctgaagga agcactaaac atgaaagga acaaccggta    4980
ccagccactg caaaaacaaa ccaaattgta aagaacattg acaccatgga gaaactgcat   5040
caactaatgg atgaaacaac cagctagcat aataatgaca gaatcaaatt cacacataac   5100
aatattaacc ttaaatgtaa acaggctaaa tgtcccaatt gaaaaacaca gactggcaaa   5160
ttagataaag tgtcaagacc catcagtgtg ctgtattcag agacccatc tcacatgcaa    5220
agacaaacat aggctcaaaa taagggatg gaggcatatt taccaagcaa atggaaaaaa    5280
aaaaaataaa gcaggagttg caatcctaat ctctgataaa accgacttta aaccaaaaaa   5340
gatcaaaaga ggcaaagaag gccattatat aatggtaaag ggatcaatgc agcaagaaga   5400
gctaactttc ctaaatatat aggcacccaa tacaggagca cccagattca taaagcaagt   5460
tctcagagac ctacaaaaaa cttagactcc cacacaataa tactgggaga ctttaacacc   5520
ccaatgttaa tattagacag atcaacgaga cagaaaatta acacagatat tcaggaactg   5580
aactcagctc tggaccaagc ggacctaata gacatctaca gaactctcca tcccaaatca   5640
```

-continued

```
acagaatata cattcttctc ggcacctcat cacacttact ttaaaactga ccacataatt    5700
ggaagtaaaa tactctgcag caaatgcaaa agaatggaag ttacaacaaa aagtttctca    5760
gaccacagtg caatcaaatt agaactcagg gttaagaaac tcactcaaaa ccacacaact    5820
acatggaaaa tgaacaacct gctcctaaat gactactggg taaataatga aatgaaggca    5880
gaaataaaga tgctctttga aaccaatgag aacaaagaca caatgtaccg gaatctctgg    5940
gacacattta aagcagtgtg tagatggaaa tttatagcat ttaatgccca caagagaaag    6000
cagaaaaaat ctaatattga cacccaaatg tcaatattaa aagaactaga gaagcaacca    6060
caaacaaatt caaaagctag cagaagaaaa gaaataacta agatcagagc agaactgaag    6120
gagatagagg catgaaaaac ccttcaaaaa aatcaatgaa tccaggaaat ggtttgttga    6180
aaagatcaac aagacagat                                                6199
```